United States Patent [19]

Moon et al.

[11] Patent Number: 5,336,673

[45] Date of Patent: Aug. 9, 1994

[54] 3-SUBSTITUTED CEPHEM COMPOUNDS

[75] Inventors: Chi J. Moon, Seongnam; Sae C. Park, Seoul; Myoung G. Kim, Seoul; Sea H. Oh, Seoul; Seong S. Yim, Seongnam; Nam J. Park, Seoul; Young K. Choi, Seongnam; Moo J. Sung, Seoul, all of Rep. of Korea

[73] Assignee: Dae Woong Pharmaceutical Co., Ltd., Seongnam, Rep. of Korea

[21] Appl. No.: 834,310

[22] PCT Filed: Apr. 19, 1991

[86] PCT No.: PCT/KR91/00012

§ 371 Date: Feb. 26, 1992

§ 102(e) Date: Feb. 26, 1992

[87] PCT Pub. No.: WO92/00981

PCT Pub. Date: Jan. 23, 1992

[30] Foreign Application Priority Data

Jul. 5, 1990 [KR] Rep. of Korea .................. 90-10143
Feb. 28, 1991 [KR] Rep. of Korea .................. 91-3397

[51] Int. Cl.5 ................ C07D 501/38; A61K 31/545
[52] U.S. Cl. .................................... 514/202; 540/222; 540/225
[58] Field of Search ........... 540/222, 225; 514/202, 514/206

[56] References Cited

U.S. PATENT DOCUMENTS

| | | | |
|---|---|---|---|
| 3,516,997 | 6/1970 | Takano et al. | 260/243 |
| 4,098,888 | 7/1978 | Ochiai et al. | 424/246 |
| 4,152,432 | 5/1979 | Heymes | 424/246 |
| 4,258,041 | 3/1981 | O'Callaghan et al. | 424/246 |
| 4,327,210 | 4/1982 | Montavon et al. | 544/27 |
| 4,329,453 | 5/1982 | Brodie et al. | 544/25 |
| 4,476,122 | 10/1984 | Heymes et al. | 424/246 |
| 4,576,938 | 3/1986 | Wagatsuma et al. | 514/206 |
| 4,921,851 | 5/1990 | Kishimoto et al. | 514/203 |
| 4,942,159 | 7/1990 | Kishimoto et al. | 514/202 |

FOREIGN PATENT DOCUMENTS 0249170 12/1987 European Pat. Off. .
0304858 3/1989 European Pat. Off. .
1384197 11/1964 France .
56-131590 10/1981 Japan .
58-72590 4/1983 Japan .
58-90590 5/1983 Japan .
58-154588 9/1983 Japan .
59-10593 1/1984 Japan .

OTHER PUBLICATIONS

Flynn et al.; *Cephalosporins and Penicillins;* Academic Press; New York, 1972; pp. 151–171.
I. Csendes et al.; *The Journal of Antibiotics;* "Cephalosporin Antibiotics"; vol. 36. (8), 1020 (1983).
Flitsch et al.; *Chem. Ber.;* "Zur Chemie 1–Amino–pyrrole"; 102, 3268 (1969).
Somie et al.; *Tetrahedron Letters;* "1–Aminoindoles"; No. 5, 461 (1974).
Stolle et al.; *Chem. Ber.;* "Uber die Konstitution der Osotetrazine und Amino–osotriazole"; 59; 1742 (1926).
Campbell et al.; *J. Chem. Soc. Commun.;* "Reactive Intermediates"; 742 (1969).
Sheng et al.; *J. Org. Chem.;* "Preparation of 1–Aminobenzimidazoles"; 28 736 (1963).
Sakai et al.; *J. Org. Chem.;* "A Rational Synthesis of 2–Aminoindazole" 37 2351 (1972).

*Primary Examiner*—Nicholas S. Rizzo
*Attorney, Agent, or Firm*—Sandler, Greenblum & Bernstein

[57] ABSTRACT

The present invention relates to novel cephalosporins of the formula (I);

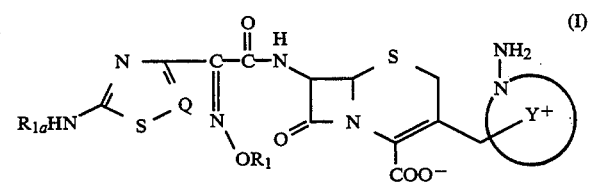

wherein,
$R_1$ represents a $C_1 \sim C_4$ alkyl group or (Abstract continued on next page.)

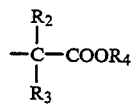

wherein, $R_2$ and $R_3$, independently, represent hydrogen or a $C_1 \sim C_3$ alkyl group and $R_4$ represents hydrogen or a $C_1 \sim C_4$ alkyl group;

$R_{1a}$ represents hydrogen or an amino-protecting group;

Q represents CH or N; and the formula

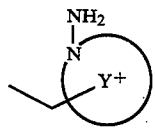

represents a saturated or unsaturated heterocyclic group which contains 1 to 4 nitrogen atoms of which one is substituted with an amino group to form quaternary ammonium, and oxygen or sulfur, or a fused heterocyclic group thereof formed together with a substituted or unsubstituted benzene or an optional heterocyclic group, or a pharmaceutically acceptable salt thereof, to processes for preparing the same and to a pharmaceutical composition containing the same as an active ingredient.

The compounds(1) according to the invention exhibit potent antibacterial activity and broad antibacterial spectrum against the Gram-positive strains including Staphylococcus as well as Gram-negative strains including Pseudomonas, and, therefore, are expected to be very useful in treatment of various diseases caused by bacterial infection in human beings and animals.

14 Claims, No Drawings

3-SUBSTITUTED CEPHEM COMPOUNDS

FIELD OF THE INVENTION

The present invention relates to novel cephalosporins and pharmaceutically acceptable salts thereof, which are useful as antibacterial agents. The invention also relates to processes for the preparation of the same, to a pharmaceutical composition containing at least one of the same as active ingredients and to a use of the same for treatment of diseases caused by bacterial infection in human beings and animals.

BACKGROUND OF THE INVENTION

Hereto, it has been known that as antibiotics a great variety of cephalosporins having the basic skeleton of the nucleus of the formula(A):

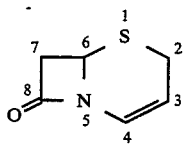

have effective antibacterial activities and are widely used as antimicrobial agents for infectious diseases caused by various Gram positive and Gram negative strains.

A variety of cephalosporins whose 7-position has 2-aminothiazolyl acetamino group substituted with α-oxyimino group have been known. Particularly, the following compounds exhibiting strong antibacterial activities against the enterobacteria have been reported: Cefotaxime in U.S. Pat. Nos. 4,152,432 and 4,098,888; Cefmenoxime in U.S. Pat. 4,098,888 and 4,476,122; Ceftriaxone in U.S. Pat. No. 4,327,210; Ceftazidime in U.S. Pat. Nos. 4,258,041 and 4,329,453.

These compounds, however, show relatively weak antibacterial activities against Staphylococcus when compared with Cephaloridine in French Patent No. 1,384,197 or Cefazoline in U.S. Pat. No. 3,516,997.

Moreover, Ceftazidime exhibits poor antibacterial activity against Staphylococcus, although its antibacterial activity against Pseudomonas is relatively stronger than that of other known cephalosporins.

The present inventors have conducted intensive research to prepare cephalosporins having improved antibacterial activities against Staphylococcus with strong antibacterial activities against Pseudomonas. As a result of prolonged studies on numerous cephalosporins, we found the 3-substituted cephem compounds show superior antibacterial activities against both of Staphylococcus and Pseudomonas.

SUMMARY OF THE INVENTION

An object of the invention is to provide novel cephalosporins represented by the formula (I):

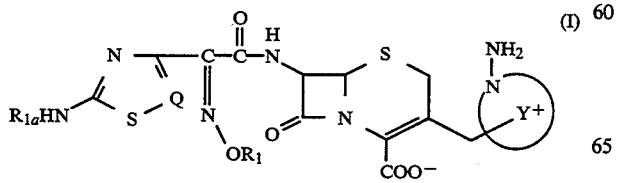

wherein, $R_1$ represents a $C_1 \sim C_4$ alkyl group or

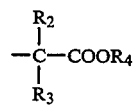

wherein, $R_2$ and $R_3$, independently, represent hydrogen or a $C_1 \sim C_3$ alkyl group and $R_4$ represents hydrogen or a $C_1 \sim C_4$ alkyl group;

$R_{1a}$ represents hydrogen or an amino-protecting group;

Q represents CH or N; and the substituent of the formula

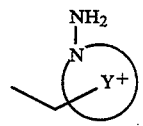

represents a saturated or unsaturated heterocyclic group containing 1 to 4 nitrogen atoms of which one must be substituted with amino group to form quaternary ammonium, and oxygen or sulfur atoms, or a fused heterocyclic group thereof formed together with a substituted or unsubstituted benzene or optional heterocyclic group, and a pharmaceutically acceptable salt thereof.

Another object of the invention is to provide processes for preparing the cephalosporins of the formula (I).

Another object of the invention is to provide pharmaceutical compositions containing at least one compound of cephalosporins as active ingradients.

Another object of the invention is to provide a use of cephalosporins of the formula (I) for treatment of the diseases caused by bacterial infection.

DETAILED DESCRIPTION OF THE INVENTION

The novel cephalosporins according to the invention may be represented by the following formula (I):

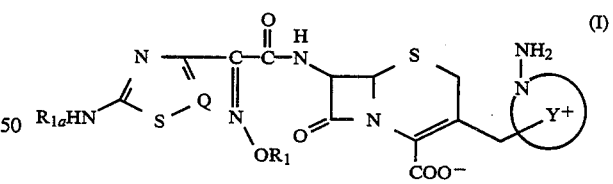

wherein, $R_1$ represents a $C_1 \sim C_4$ alkyl group or

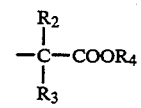

wherein, $R_2$ and $R_3$, independently, represent hydrogen or a $C_1 \sim C_3$ alkyl group and $R_4$ represents hydrogen or a $C_1 \sim C_4$ alkyl group;

$R_{1a}$ represents hydrogen or an amino-protecting group;

Q represents CH or N; and the formula

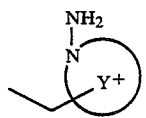

represents a saturated or unsaturated heterocyclic group containing 1 to 4 nitrogen atoms of which one must be substituted with an amino group to form quaternary ammonium, and oxygen or sulfur atoms, or a fused heterocyclic group thereof formed together with a substituted or unsubstituted benzene or optional heterocyclic group.

The examples of the 3-position substituent

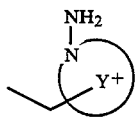

may include
1-aminopyrrolidinium methyl,
1-aminopiperidinium methyl,
(4-aminomorpholin-4-ium)methyl,
(1-amino1,2,3,6-tetrahydropyridinium)methyl,
(1-amino-3-pyrrolin-1-ium)methyl,
1-aminoindolinium methyl,
1-aminopyrrolium methyl
1-aminoindolium methyl
(1-amino-4-hydroxypiperidinium)methyl,
(2-amino-1,2,3,4-tetrahydroisoquinolin-2-ium)methyl,
(1-amino-1-methyl-4-piperazinium)methyl,
(4-amino-1,2,4-triazol-2-ium)methyl,
(1-amino-1,2,3-triazol-3-ium)methyl,
(1-amino-1,2,4-triazol-4-ium)methyl,
(1-aminobenzotriazol-3-ium)methyl,
(1-aminobenzimidazol-3-ium)methyl,
(1-aminoimidazol-3-ium)methyl,
(1-aminopyrazol-2-ium)methyl,
(1-aminotetrazol-4-ium)methyl,
(1-amino-1,4,5,6-tetrahydropyrimidin-3-ium)methyl and
(1-aminoindazol-2-ium)methyl.

The C-7 position of the formula (I) may be represented by

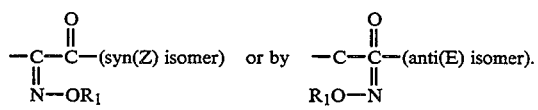

However, generally, the syn isomer is preferred. For the present invention, both of the starting materials and the products are syn isomer.

The pharmaceutically acceptable salts of the compounds (I) are conventional non-toxic salts and may include an inorganic acid salt (e.g., sulfate, hydrochloride, hydrobromide, iodide, phosphate etc.), an organic carboxylic acid salt (e.g., acetate, malcate, tartrate, fumarate, citrate, succinate, malate, lactate, oxalate, etc.), a sulfonic acid salt (e.g. methanesulfonate, benzenesulfonate, p-toluenesulfonate, etc.), a salt with a basic, or acidic amino acid (e.g., salts with arginine, asparagine, glutamine, lysine, etc.), an inorganic salt, for example, metal salts such as an alkali metal salt (e.g., sodium salt, potassium salt), and an alkaline earth metal salt (e.g. magnesium salt), an ammonium salt, and an organic salt, (e.g., trimethylamine salt, triethylamine salt, pyridine salt, procaine salt, picoline salt, dicyclohexylamine salt, N-methylglucamine salt, diethanolamine salt, triethanolamine salt, phenylethylbenzylamine salt, dibenzylethylenediamine salt, etc.).

For the present invention, an inorganic acid salt such as sulfate or hydrochloride and an organic acid salt such as maleate or fumarate are particularly preferred since they are formed stable crystalline salts of the cephalosporins(I)

According to the present invention, processes for preparing the cephalosporins(I) and pharmaceutically acceptable salts thereof are provided.

The cephalosporins according to the invention may be prepared by the following processes:

The First reaction scheme:

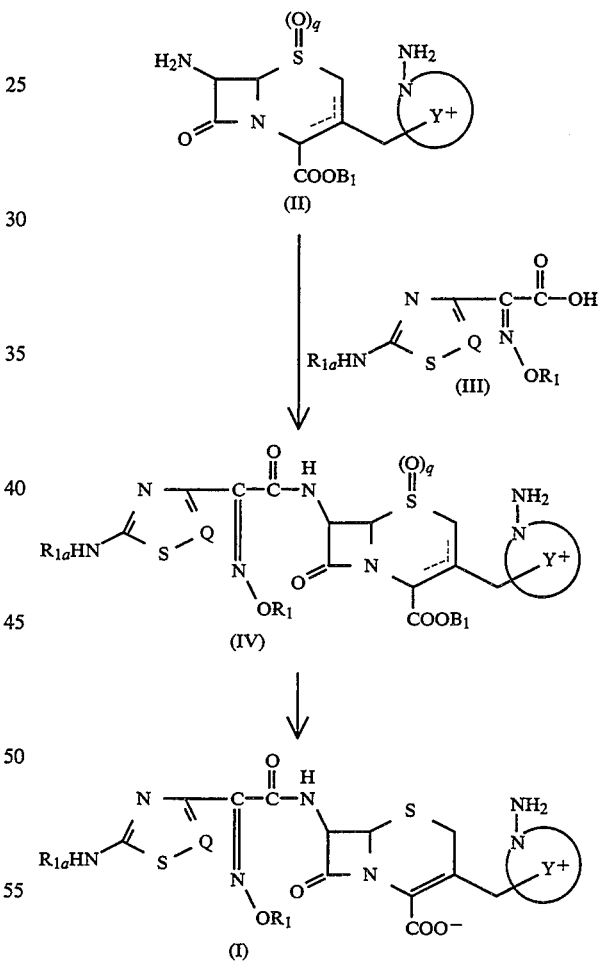

Wherein, $R_1$ and Q are the same as defined above;

$R_{1a}$ represents hydrogen or an amino-protecting group;

$B_1$ represents hydrogen or a carboxyl-protecting group;

q represent integer of 0 or 1;

the formula

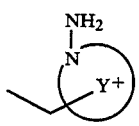

is the same as defined above; and the dotted line means ceph-2-em or ceph-3-em compound.

In the first reaction scheme, the compound of the formula (II) as an intermediate may be synthesized by the following procedure:

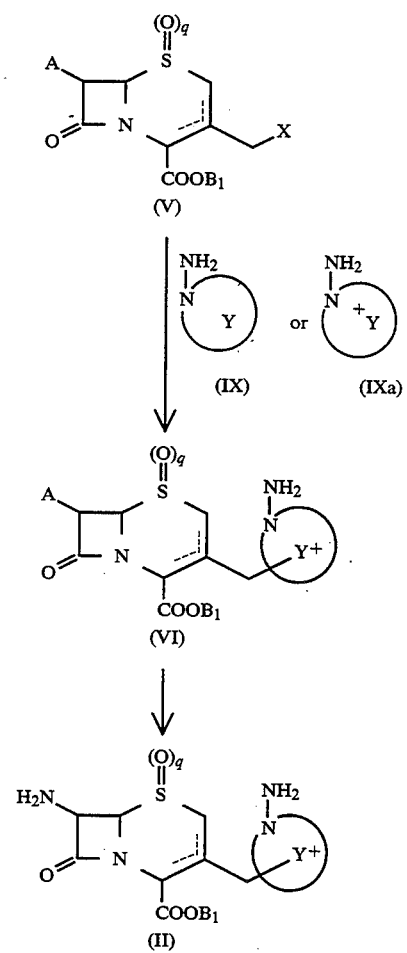

Wherein,
$B_1$, q,

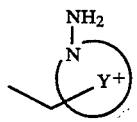

and the dotted line are the same as defined above;

X represents a leaving group, which is halogen or an acetoxy group; and

A represents an amine or imine group which are protected by amino protecting groups.

The second reaction scheme:

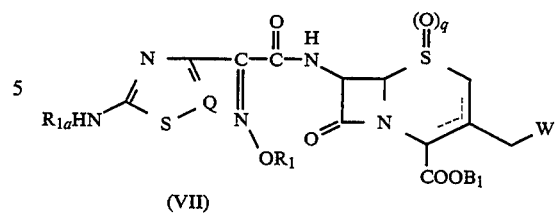

(VII)

↓ (IX) or (IXa)

(IV)

↓

(I)

Wherein,
$R_1$, $R_{1a}$, Q, $B_1$, q, and the dotted line are the same as defined above; and
W represents a residue which may be substituted with a nucleophile.

In preparing the compounds of the formula (I) according to the first or second reaction scheme, any of the following steps can be suitably conducted, if necessary:

(i) Removing of carboxyl- or amino-protecting group
(ii) Conversion of $\Delta^2$ isomer to $\Delta^3$ isomer, or vice versa
(iii) Conversion(Reduction) of sulfoxide compound (q=1) to sulfide compound (q=0)
(iv) Formation of non-toxic salt Preferred compounds of the formula (II) and (VII) in the above first or second reaction scheme are those compounds in which q is 0 and the dotted line represents ceph-3-em.

$\Delta^2$ cephalosporin ester derivative (q=1) obtained according to the process of the invention may be converted to $\Delta^3$ cephalosporin ester by treating with base such as triethylamine or pyridine. In case that sulfoxide compound (q=1) is obtained, it may be converted to the sulfide compound by treating with reducing agent such as sodium dithionite.

The amino- or carboxyl-protecting group may be suitably selected from the conventional protecting groups which are commonly employed in the technical field of β-lactam and peptide synthesis.

The amino-protecting group may include phthaloyl, formyl, monochloroacetyl, dichloroacetyl, trichloroacetyl, methoxycarbonyl, ethoxycarbonyl, t-butoxycarbonyl, trichloroethoxycarbonyl, benzyloxycarbonyl, p-nitrobenzyloxycarbonyl, diphenylmethyloxycarbonyl, methoxymethyloxycarbonyl, trityl, trimethylsilyl, phenylacetyl, salicyl, benzoyl and the like.

The carboxyl-protecting group may be include t-butyl, t-amyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, trichloroethyl, trimethylsilyl, dimethylsilyl, dimethylaminoethyl and the like.

The compounds of the formula (II) can be prepared by the method described in Llynn et al., Cephalosporins and penicillin, Academic Press, p 151~171 (1972). For example, they can be prepared by reacting 7β-acylamino-3-halomethyl-3-cephem-4-carboxylate derivatives disclosed in Japanese Patent Unexamined Publication Nos. 83-72590 or 83-154588 with the compounds of the formula (IX) or (IXa).

The compounds of the formula (II) also can be prepared by a conventional method using acids, for example, trifluoroacetic acid, formic acid, conc.hydrochloric acid or phosphorus halide (e.g., phosphorous pentachloride, phosphorus oxychloride, etc.).

The acylation in the first reaction scheme is conducted by reacting 1 mole of the compound(II) with 1 to 3 moles of carboxylic reactive derivative of the compound(III). The examples of the reactive derivatives may include an acid halide, an acid anhydride, an active amide, an active ester and the like. Preferred examples are an acid halide such as acid chloride or acid bromide, a mixed acid anhydride such as acetic acid, pivalic acid, isopivalic acid or trichloroacetic acid, an active amide such as pyrazole, imidazole, dimethylpyrazole or benzotriazole, and an active ester such as p-nitrophenylester, 2,4-dinitrophenylester, trichlorophenylester, 1-hydroxy-1H-2-pyridone, N-hydroxysuccinimide or N-hydroxyphthalide.

The acylation is preferrably conducted in the presence of condensing agents in case that the compounds(III) are a free acid form. The examples of the condensing agent may include a carbodiimde compound such as N,N-dicyclohexylcarbodiimide, N-cyclohexyl-N'-morpholinoethylcarbodiimide, N-cyclohexyl-N'-(4-diethylaminocyclohexyl)carbodiimide and the like. The acylation also may be conducted in the presence of Vilsmeier reagents formed from the reaction of amide compounds such as N-methylformamide or N,N-dimethylformamide with halides such as thionyl chloride, phosphorus oxychloride or phosgene.

When acid halides or acid anhydrides are used as reactive derivatives, it is necessary to conduct acylation in the presence of acid condensing agents, for example an organic base such as triethylamine, trimethylamine, ethyldiisopropylamine, N,N-dimethylamine, N-methylmorpholine or pyridine, an alkali metal compound such as hydroxide, carbonate or bicarbonate of sodium, potassium or calcium, and oxylan such as ethylene oxide or propylene oxide.

The reaction is carried out in the presence of the solvents which do not influence the reaction adversely. The examples of the solvent may include water, acetone, acetonitrile, dioxane, tetrahydrofuran, dichloromethane, chloroform, dichloroethane, N,N-dimethylformamide or mixtures thereof.

The reaction temperature is not specifically limited, but generally ranges between −30° C. and 40° C.

The reaction time generally ranges between 30 min and 10 hours.

The protecting group should be removed in case that the acylated product has a protecting group. The method for removing the protecting group may be suitably selected according to the kind of the protecting group from the methods using an acid, methods using a base or methods using a hydrazine, which are generally used in the field of β-lactam and peptide synthesis.

With regard to the process of the second reaction scheme, the example of the residue W may include an acetoxy group and a halogen atom such as chlorine, bromine or iodine.

The compounds of (VII) wherein Q is N, $B_1$ is hydrogen and W is an acetoxy group may be prepared by a method described in The Journal of Antibiotics, Vol. 36(8), 1020(1983).

The reaction of the compounds (VII) wherein W is an acetoxyl group with the compounds (IX) or (IXa) is preferrably carried out in the polar solvents, for example, water, phosphate buffer, acetone, acetonitrile, N,N-dimethylformamide, N,N-dimethylacetamide, tetrahydrofuran, dimethylsulfoxide, dioxane, methanol or ethanol and mixtures thereof with water.

The reaction is preferrably carried out around the neutral pH.

The reaction temperature is not specifically limited, but is preferrably 15° C. to about 70° C.

The reaction time varies depending on the reaction conditions, but is generally 1 to 10 hours.

The reaction may be accelerated by adding alkali metal halides, for example, sodium iodide, lithium iodide or potassium iodide to the reaction mixture.

In case that the compounds (VII) wherein W is a halogen are used to prepare the desired compounds (I), the halogen may include chlorine, bromine and iodine. The halide compounds are easily prepared by methods in Japanese Patent Unexamined Publication Nos. 81-131,590, 83-90,590 and 84-10,593.

The reaction is preferrably carried out in the presence of a solvent such as acetone, dichloromethane, acetonitrile, N,N-dimethylformamide or N,N-dimethylacetamide under the non-aqueous condition.

The reaction temperature is preferrably 0° to 50° C. and the reaction time is generally 1 to 5 hours.

The protecting group can be removed by known methods to give the compounds(I).

The compounds(IX) or (IXa) which will be introduced into 3-position of the cephem nucleus as substituents are commercially available. For example, 1-aminopyrrolidine, 4-aminomorpholine, 1-aminopiperidine and 4-amino-1,2,4-triazole were purchased from Aldrich. They also may be synthesized by the known methods. For example, 1-aminopyrrole, 1-aminoindole, 1-amino-1,2,3-triazole, 1-aminobenzotriazole, 1-aminobenzimidazole and 1-aminoindazole were prepared by methods described in Flitsch, W. et al., Chem. Ber., 102, 3268 (1969), Masanori, N. et al., Tetrahedron Lett., 461 (1974), Stolle, R. et al., Chem. Ber., 59, 1742 (1926), Campbell, C. D. et al., J. Chem. Soc. Chem.

Commun., 742 (1969), Sheng, M. N. et al., J. Org. Chem., 28, 736 (1963) and Sakai, K. et al., J. Org. Chem., 37, 2351 (1972), respectively.

Further, for example, 1-amino-1,2,3,6-tetrahydropyridine, 1-amino-3-pyrroline, 1-aminoindoline, 1-aminohydroxypiperidine, 2-amino-1,2,3,4-tetrahydroisoquinoline, 1-amino-1,2,4-triazole, 1-aminoimidazole, 1-aminopyrazole, 1-aminotetrazole and 1-amino-1,4,5,6-tetrahydropyrimidine also may be prepared by the above methods. Alternatively, they also may be prepared by reacting 1,2,3,6-tetrahydropyridine, pyrroline, indoline, hydroxypiperidine, 1,2,3,4-tetrahydroisoquinoline, 1,2,4-triazole, imidazole, pyrazole or tetrazole with hydroxylamine-O-sulfonic acid or chloramine-T in the presence of an inorganic salt in water or a mixed solvent of water and an organic solvent(1:1~3:1). If necessary, they may be separated and purified by silica gel column chromatography.

The organic solvents are of water-miscible and may be suitably selected from N,N-dimethylformamide, N,N-dimethylformacetamide, methanol, ethanol, acetone, acetonitrile or dioxane.

The inorganic salt may be suitably selected from sodium hydroxide, potassium hydroxide, calcium carbonate or sodium hydride.

Particularly, in case that the 3-position substituent is 1-amino-1-methylpiperazinium, the amino group of 1-methylpiperazine is protected by a conventional amino-protecting group, for example, acetyl, benzyloxycarbonyl or t-butoxycarbonyl group. Then, thus obtained amino-protected 1-methylpiperazine is reacted with hydroxylamine-O-sulfonic acid in the presence of an inorganic solvent in water or a mixed solvent of water and an organic solvent to give amino-protected 1-amino-1-methylpiperazinium and the amino-protecting group is deprotected to give the desired compound.

When the heterocyclic compound having two or more nitrogen atoms as a hetero atom, for example, 4-amino-1,2,4-triazole, 1-amino-1,2,3-triazole, 1-amino-1,2,4-triazole, 1-aminopyrazole, 1-aminotetrazole, 1-amino-1,4,5,6-tetrahydropyrimidine, 1-aminobenzotriazole, 1-aminobenzimidazole, 1-aminoindazole or 1-aminoimidazole is introduced into 3-position of the cephem nucleus, the compounds of the formula(I) may exist in tautomeric forms and such tautomers are the equivalent and also included within the scope of the invention. Namely, the position of the positive charge varies depending on the state of salt, the kind of solvent, the properties of solution, the temperature, the kind of substituent and the like, as follows:

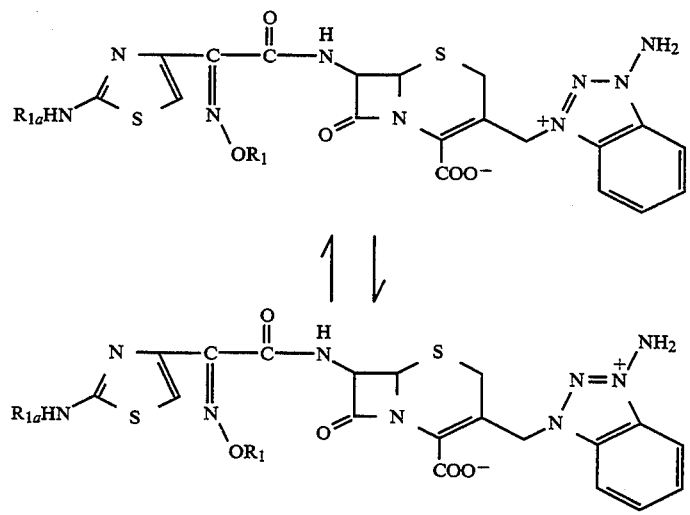

The salts of the compounds (I) according to the invention can be prepared by dissolving the compounds of the formula (I) in an aqueous solution of inorganic or organic acid, preferrably an aqueous solution containing 1 to 10 equivalents of inorganic or organic acid, stirring the solution at 0°~5° C. for 5 to 10 hours, then precipitating to give a crystalline salt of compound (I).

The compounds (I) and salts thereof according to the invention are novel cephalosporins and exhibit potent and broad antibacterial activities against a variety of pathogenic bacteria including Gram-positive and negative strains, particularly against Staphylococcus and Pseudomonas.

In order to illustrate the pharmaceutical usefulness of the compounds (I) of the invention, the representative examples of compounds (I) were teseted for their antibacterial activities against the standard test strains and the clinically isolated strains.

The antibacterial activity was determined by an Agar dilution method as described below.

That is, the two-fold serial dilutions of the antibacterial compounds (1000 μg compound/ml) were prepared and dispersed in Muller Hinton Agar in a petri dish to a concentration of 100~0.002 μg/ml. The culture broths of standard test strains were inoculated on the medium to a concentration $10^7$ CFU/ml, and incubated at 37° C. for 18 hours. The concentration of compounds(I) at which the strains were not grown was regarded as minimum inhibition concentration (MIC).

The results of antibacterial activity test of the representative examples of the compound (I) against 20 standard test strains shown in terms of MIC were indicated in Table 1.

The MIC of the compound of Example 18 against 254 clinically isolated strains were shown in Table 2.

The representative examples of the compounds (I) according to the invention are as follows:

Compound of Example 1: (6R,7R)-7-[(Z)-2-(2-aminothiazol-4-yl)-2-methoxyiminoacetamido]-3-(1-aminopyrrolidiniummethyl)ceph-3-em-4-carboxylate Compound of Example 5: (6R,7R)-7-[(Z)-2-(2-aminothiazol-4-yl)-2-methoxyiminoacetamido]-3-[(2-amino- 1,2,3,4-tetrahydroisoquinolin-2-ium)methyl]-ceph-3-em-4-carboxylate Compound of Example 11: (6R,7R)-7-[(Z)-2-(2-aminothiazol-4-yl)-2-methoxyiminoacetamido]-3-[(1-amino-1-methyl-4-piperazinium)methyl]-ceph-3-em-4-carboxylate Compound of Example 12: (6R,7R)-7-[(Z)-2-(2-aminothiazol-4-yl)-2-methoxyiminoacetamido]-3-[(4-amino-1,2,4-triazol-2-ium) methyl]-ceph-3-em-4-carboxylate Compound of Example 18: (6R,7R)-7-[(Z)-2-(2-aminothiazol-4-yl)-2-methoxyiminoacetamido]-3-[(1-aminobenzotriazol-3-ium) methyl]-ceph-3-em-4-carboxylate Compound of Example 19: (6R,7R)-7-[(Z)-2-(2-aminothiazol-4-yl)-2-methoxyiminoacetamido]-3-[(1-aminobenzimidazol-3-ium) methyl]-ceph-3-em-4-carboxylate Compound of Example 36: (6R,7R)-7-[(Z)-2-(2-aminothiazol-4-yl)-2-(2-carboxyprop-2-oxyimino)acetamido]-3-[(4-amino-1,2,4-triazol-2-ium)methyl]-ceph-3-em-4-carboxylate Compound of Example 85: (6R,7R)-7-[(Z)-2-(5-amino-1,2,4-thiadiazol-3-yl)-2-methoxyiminoacetamido]-3-[(1-aminobenzotriazol-3-ium)methyl]-ceph-3-em-4-carboxylate Cefotaxime-Sodium was used as a control.

20 standard test strains used in the present invention are pathogenic strains causing various infections such as urinary tract infection, respiratory track infection, dermal soft tissue infection, blood plasma infection, stomach-instestine infection or central nerve system infection, and most of them are β-lactamase producing strains. They are shown below:

Gram-positive bacteria
1. *Streptococcus pyogenes* A 308
2. *Streptococcus pyogenes* A 77
3. *Streptococcus faecium* MD 86
4. *Staphylococcus aureus* SG 511
5. *Staphyloccus aureus* 285
6. *Staphylococcus aureus* 503

Gram-negative bacteria
7. *Escherichia coli* O 55
8. *Escherichia coli* DC 0
9. *Escherichia coli* DC 2
10. *Escherichia coli* TEM
11. *Escherichia coli* 1507E
12. *Pseudomonas aeruginosa* 9027
13. *Pseudomonas aeruginosa* 1592E
14. *Pseudomonas aeruginosa* 1771
15. *Pseudomonas aeruginosa* 1771M
16. *Salmonella typhimurium*
17. *Klebsiella oxytoca* 1082E
18. *Klebsiella aerogenes* 1522E
19. *Enterobacter cloacae* P99
20. *Enterobacter cloacae* 1321E

TABLE 1

Antibacterial activity of compounds (I) against the standard test strains; MIC (μg/ml)

| No. of tested strain | compound (No. of Example) | | | | | | | | Cefotaxime |
|---|---|---|---|---|---|---|---|---|---|
| | 1 | 5 | 11 | 12 | 18 | 19 | 36 | 85 | |
| 1 | 0.025 | 0.049 | 0.013 | 0.007 | 0.004 | 0.013 | 0.098 | 0.007 | 0.007 |
| 2 | 0.025 | 0.013 | 0.007 | 0.007 | 0.004 | 0.007 | 0.049 | 0.004 | 0.004 |
| 3 | >100 | 50 | >100 | >100 | >100 | >100 | 25 | 100 | 100 |
| 4 | 6.258 | 1.563 | 1.563 | 1.563 | 0.391 | 0.781 | 1.563 | 0.391 | 1.563 |
| 5 | 12.5 | 6.250 | 12.5 | 3.125 | 0.781 | 0.781 | 3.125 | 1.563 | 1.563 |
| 6 | 1.563 | 0.781 | 0.781 | 0.781 | 0.195 | 0.391 | 1.563 | 0.391 | 0.781 |
| 7 | 0.195 | 0.391 | 0.195 | 0.025 | 0.007 | 0.098 | 0.195 | 0.007 | 0.007 |
| 8 | 0.195 | 0.391 | 0.781 | 0.098 | 0.025 | 0.391 | 0.781 | 0.025 | 0.025 |
| 9 | 0.391 | 0.781 | 0.781 | 0.097 | 0.025 | 0.391 | 0.195 | 0.025 | 0.013 |
| 10 | 0.391 | 0.781 | 0.391 | 0.049 | 0.013 | 0.391 | 3.125 | 0.025 | 0.025 |
| 11 | 0.391 | 0.781 | 0.781 | 0.098 | 0.025 | 0.391 | 1.563 | 0.049 | 0.025 |
| 12 | 100 | 50 | 50 | 12.5 | 3.125 | 50 | 6.25 | 3.125 | 12.5 |
| 13 | 100 | 50 | 50 | 6.25 | 1.563 | 25 | 6.25 | 3.125 | 12.5 |
| 14 | 50 | 50 | 25 | 6.25 | 1.563 | 12.5 | 1.563 | 1.563 | 6.25 |
| 15 | 3.125 | 1.563 | 1.563 | 0.195 | 0.781 | 0.781 | 0.098 | 1.563 | 0.098 |
| 16 | 0.781 | 0.781 | 0.391 | 0.098 | 0.195 | 0.195 | 6.250 | 0.195 | 0.025 |
| 17 | 12.5 | 12.5 | 6.250 | 1.563 | 0.049 | 3.125 | 100 | 0.781 | 0.781 |
| 18 | 0.195 | 0.013 | 0.391 | 0.049 | 0.025 | 0.195 | 0.781 | 0.049 | 0.013 |
| 19 | >100 | 100 | 100 | 100 | 12.5 | >100 | 100 | 25 | 100 |
| 20 | 0.098 | 0.013 | 0.195 | 0.025 | 0.007 | 0.195 | 0.391 | 0.007 | 0.013 |

TABLE 2

Antibacterial activity of the compound of Example 18 against clinically-isolated strains

| Strains (No. of tested) | MIC (μg/ml) | | |
|---|---|---|---|
| | Range | 50% | 90% |
| *Enterobacter cloacae* (20) | 0.007–12.5 | 0.025 | 0.391 |
| *Escherichia coli* (20) | 0.007–0.195 | 0.013 | 0.025 |
| *Serratia* spp (20) | 0.013–0.098 | 0.025 | 0.049 |
| D Streptococcus I (20) | 3.125–100 | 12.5 | 100 |
| D Streptococcus II (20) | 3.125–100 | 25 | 50 |
| *Pseudomonas aeruginosa* (20) | 1.563–25 | 6.25 | 12.5 |
| Pseudomonas I (19) | 0.195–12.5 | 1.563 | 6.25 |
| Pseudomonas II (19) | 0.391–12.5 | 1.563 | 6.25 |
| Streptococcus I (20) | 0.004–12.5 | 0.025 | 6.25 |
| Streptococcus II (17) | 0.002–0.013 | 0.004 | 0.007 |
| Enterococcus I (20) | 0.007–0.195 | 0.025 | 0.049 |
| Enterococcus II (20) | 0.004–25 | 0.025 | 0.098 |
| *Morganella morganil* (5) | 0.004–0.025 | 0.013 | 0.025 |
| *Providencia rettgeri* (6) | 0.007–0.195 | 0.025 | 0.098 |
| *Proteus mirabilis* (4) | 0.013–0.098 | 0.013 | 0.098 |
| *Proteus vulgaris* (5) | 0.025–0.195 | 0.098 | 0.195 |

As shown in Table 1, the compounds(I) of the invention exhibit broader antibacterial spectrum and more potent antibacterial activity against Gram-negative and positive strains in comparison with Cefotaxime-Sodium. Particularly, the compound of Example 18 exhibits superior activity against β-lactamase producing strains such as *Pseudomonas aeruginosa* and *Enterobacter cloacae* which have clinical problems in the field of cephem antibiotics as well as show strong activity against Gram-positive strains, for example, *Staphylococcus aureus* which is resistant to the third-generation cephalosporins.

The compounds of Examples 1, 5, 11, 12, 19 and 36 also exhibited excellent antibacterial activity against Gram-positive strains as well as against Gram-negative strains including Pseudomonas.

Particularly, the compounds of Examples 12, 18, 36 and 85 are expected to be very useful for treatment of an intractable infection diseases caused by Staphylococcus or Pseudomonas.

In order to establish the usefulness in clinical applications of the compounds provided by the invention, the compound of Example 18 was tested for stability against the β-lactamase and for antibacterial activity on systemic infection model.

First, the stability against the β-lactamase was tested by determining the relative(percentage) hydrolysis of the compound of Example 18, relative to that of Cephaloridine, taking the absolute rate of Cephaloridine as 100.

The β-lactamases employed in the test were directly isolated from *Enterobacter cloacae* P99, *E. coli* TEM and *Citrobacter freundii*, and the antibiotics for comparison were Cephaloridine, Cephradine, Cefoperazone and Cefotaxime.

Cephaloridine, other known antibiotics and the compound of Example 18 were reacted with each of the enzymes isolated from the strains and the OD were determined at 260 nm, λmax of Cephaloridine. The relative hydrolysis of various compounds were calculated relative to the OD of Cephaloridine. The results were shown in Table 3.

TABLE 3

| Antibiotics (100 μM) | Relative hydrolysis by β-lactamase | | |
|---|---|---|---|
| | Source of β-lactamase | | |
| | *Enterobacter cloacae* P99 | *E. coli* TEM | *Citrobacter freundil* |
| Cephaloridine | 100 | 100 | 100 |
| Cephradine | 14.9 | 0.8 | 13.6 |
| Cefoperazone | 1.4 | 38.6 | 1.2 |
| Cefotaxime | 0.0 | 0.6 | 0.6 |
| Compound of Example 18 | 0.0 | 0.0 | 0.2 |

The antibacterial activity test on systemic infection model was carried out using the compound of Example 18 as follows: 0.3 ml of diluted solution containing lethal dose of strain was administered intraperitoneally to the test animal, and then 5 to 0.078 mg/kg of compound was administered intramuscularly. The $PD_{50}$ was calculated by T probit method and the result was shown in Table 4.

TABLE 4

| Treatment effect on systemic infection model | |
|---|---|
| Tested strain | $PD_{50}$ (mg/kg) (The limit of confidence)* |
| *Streptococcus pyogenes* 77A | 0.27 (0.08~0.47) |

*P<0.05

Further, in order to illustrate the usefulness of the compounds (I) as a drug, compounds of Examples 12, 18 and 36 were tested for acute toxcity by using 4 weeks-old male ICR-mouse as a test animal.

the compounds were dissolved in physiological saline and phosphate buffered solution (pH 7.0), or if they were hot soluble, suspended in carboxymethylcellulose or gum Arabic and then mixed with phosphate buffered solution.

The solution or mixture was administered to the tested animals intravenously or subcutaneously and, after 1 week, the number of surviving animals was calculated.

The results of the acute toxcity test were shown in Table 5.

TABLE 5

| Compound (No. of Example) | Acute toxcity test | |
|---|---|---|
| | $LD_{50}$ mg/kg | |
| | Intravenous administration | Subcutaneous administration |
| 12 | >4000 | >6000 |
| 18 | >4000 | >6000 |
| 36 | >4000 | >6000 |

As shown in the Table 5, the $LD_{50}$ of the tested compounds are more than 4000 mg/kg when intravenously administered and more than 6000 mg/kg when subcutaneously administered, so that it was demonstrated that their safty as a drug was very high.

As described above, the compounds according to the present invention exhibit potent and broad antibacterial activity against Gram-positive strains as well as Gram-negative strains including Pseudomonas, while its toxcity is very low.

The compounds of the invention may be administered parenterally for treatment of bacterial infection in human beings in a dose of 50~1000 mg, preferrably 100~500 mg per adult, 2~4 times a day, preferrably.

The pharmaceutical composition according to the invention contains the compounds (I) as an active ingredient in association with solid or liquid excipients. The excipients may include those one which are commonly employed in the filed of antibiotic pharmaceutics.

The pharmaceutical composition may be formulated into solid formulations, for example, tablet, capsule or powder, or liquid formulations, for example, injection solution, suspension or syrup. The liquid formulations are preferred.

The present invention will be described in detail with reference to the following examples, but is not limited thereto.

REFERENCE EXAMPLE 1

Synthesis of 1-amino-1,2,3,6-tetrahydropyridine

To a mixed solvent of water(40 ml) and methanol(10 ml) was added 11.06 g(80 mmol) of potassium carbonate, and 3.65 ml(40 mmol) of 1,2,3,6-tetrahydropyridine and 4.52 g(40 mmol) of hydroxylamine-O-sulfonic acid were added thereto. The mixture was stirred at room temperature for 4.5 hours and concentrated under the reduced pressure to the half of its original volume. The resulting solid was filtered off and the filtrate was extracted with dichloromethane. The organic layer was treated with anhydrous magnesium sulfate and filtered. The filtrate was concentrated under the reduced pressure and then subjected to chromatography over silica gel using 10% methanol/dichloromethane as an eluent to give 1.77 g of the desired compound(45%).

Rf=0.5 (in 10% methanol/dichloromethane)

NMR ($D_2O$, δ)

2.12~2.48 (m, 2H), 3.20 (t, 2H) 3.42~5.91 (m, 2H)

REFERENCE EXAMPLE 2

Synthesis of 1-amino-3-pyrroline

To 20 ml of water was added 0.69 g(10 mmol) of 3-pyrroline and 1.68 g(30 mmol) of potassium hydroxide was added thereto under stirring. 1.7 g(15 mmol) of hydroxylamine-O-sulfonic acid was added while cooling the mixture to 5° C. or below. The reaction mixture was stirred at 40°~50° C. for 3 hours, cooled and the pH was adjusted to 7~8. Then, it was concentrated under the reduced pressure to remove water.

To the residue was added methanol. After stirring for 10 min, the solid was filtered off and the filtrate was dried over anhydrous magnesium sulfate. Concentration under the reduced pressure gave 0.4 g of the desired compound(17%).

Rf=0.5 (in 10% methanol/dichloromethane)

NMR (DMSO-$d_6$, δ) 2.72~4.21 (br, 2H, $NH_2$), 4.54(s, 4H) 5.92 (s, 2H)

REFERENCE EXAMPLE 3:

Synthesis of 1-aminoindoline

In 40 ml of water was dissolved 2.76 g(20 mmol) of potassium carbonate thoroughly, and 10 ml of acetonitrile and 2.24 ml(20 mmol) of indoline were added thereto in this order. After stirring the reaction mixture for 10 min, 2.26 g(20 mmol) of hydroxylamine-O-sulfonic acid was added thereto. After stirring at room temperature for 1.5 hours, the reaction mixture was concentrated under the reduced pressure. The concentrate was extracted with dichloromethane and treated with anhydrous magnesium sulfate. After filtration, the filtrate was concentrated under the reduced pressure, and the resulting concentrate was subjected to chromatography over silica gel using dichloromethane as an eluent. The fractions were concentrated to give 0.99 g of the desired compound(37%).

Rf=0.17 (in dichloromethane)

NMR (DMSO-$d_6$, δ) 2.73~3.06 (m, 2H, —$CH_2$—), 3.25~3.68 (m, 2H,$NH_2$) 4.10~6.3 (br, 2H, N—$CH_2$—), 6.71~7.01 (m, 2H) 7.02~7.29 (m, 2H)

REFERENCE EXAMPLE 4

Synthesis of 1-aminoindole

To 50 ml of N,N-dimethylformamide were added 24.55 g(440 mmol) of potassium hydroxide and 3.201 g(27.3 mmol) of 1H-indole, and 6.15 g (54.4 mmol) of hydroxylamine-0-sulfonic acid was added thereto in small amounts under stirring. After stirring the reaction mixture at room temperature for 1 hour, 50 ml of water was added thereto and it was extracted three times with 100 ml of benzene. The extract was washed with water, dried and concentrated under the reduced pressure. Silica gel column chromatography of the residue using 50% dichloromethane/n-hexane as an eluent gave 1.16 g of the desired compound(32%).

m.p.=41°~41.5° C.

NMR (CDCl$_3$, δ) 4.73 (br, 2H, $NH_2$), 6.37 (d, 1H) 7.01~7.65 (m, 5H, phenyl)

REFERENCE EXAMPLE 5

Synthesis of 1-aminopyrrole

To 10.0 g(61.7 mmol) of N-aminophthalimide was added a solution of 12 ml(72.4 mmol) of 2,5-diethoxytetrahydrofuran in 100 ml of dioxane and 10 ml of 5 N hydrochloric acid was added thereto. The reaction mixture was stirred for 1 hour and cooled to 5° C. The resulting precipitate was filtered, recrystallized from dioxane:water(1:3), washed with ethanol and dried to give 10.3 g of 1-phthalimidopyrrole. This product was dissolved in 60 ml of methanol and 3 ml of 82% hydrazine hydrate was slowly added thereto. After refluxing the reaction mixture for 30 min, cooled to 0°~5° C. and 1.5 ml of glacial acetic acid was added thereto. The resulting precipitate was filtered off and the filtrate was concentrated under the reduced pressure to remove methanol. The concentrate was washed with diethyl ether and vacuum-distilled to give 2.4 g of the desired compound(47.3%).

bp=71°~73° C. (12 mmHg)

NMR (CDCl$_3$, δ) 4.5 (s, 2H, $NH_2$), 5.89 (t, 2H) 6.40 (t, 2H)

REFERENCE EXAMPLE 6

Synthesis of 1-amino-4-hydroxypiperidine

In 10 ml of water was dissolved 0.6 g(6 mmol) of hydroxylamine-O-sulfonic acid and 1.82 g(1.8 mmol) of 4-hydroxypiperidine was added thereto. After refluxing for 1 hour, the reaction mixture was cooled to 5° C. and 0.84 g(6.1 mmol) of potassium carbonate was added thereto. The reaction mixture was stirred for 10 min and the precipitate was filtered off. The filtrate was concentrated under the reduced pressure and 15 ml of dry ethanol was added to give precipitate, which was filtered off. While cooling the filtrate to 5°~10° C., 0.85 ml of 57% HI was slowly added and the mixture was stirred at the same temperature for 30 min. To the reaction mixture was added 50 ml of petroleum ether. The filtrate was washed with acetone to give 1.41 g of the desired compound(34%).

m.p.=117°-119° C.

NMR (DMSO-$d_6$, δ) 1.12~1.98 (m, 4H), 2.41~2.86 (m, 2H) 2.86~3.24 (m, 2H), 3.40~3.79 (m, 1H) 5.23 (br, 2H, $NH_2$)

REFERENCE EXAMPLE 7

Synthesis of 2-amino-1,2,3,4-tetrahydroIsoquinoline

In a mixed solvent of 50 ml of water and 20 ml of methanol was dissolved 11.06 g (80 mmol) of potassium carbonate and 5.33 g (40 mmol) of 1H-1,2,3,4-tetrahydroisoquinoline and 4.52 g (40 mmol) of hydroxylamine-O-sulfonic acid were added thereto while maintaining the temperature at 30° C. The mixture was stirred at room temperature for 4 hours. After completion of reaction, the insoluble was filtered off and the filtrate was extracted twice with dichloromethane. The dichloromethane layer was dried over anhydrous magnesium sulfate and concentrated to driness. The resulting residue was subjected to silica gel column chromatography using 5% methanol/dichloromethane as an eluent. The fractions containing the desired product were concentrated under the reduced pressure and crystallized from tetrahydrofuran to give 1.78 g of the desired compound in a form of white crystal (30%).

m.p.=179°~181° C.

NMR (DMSO-$d_6$+10% DCl, δ) 2.95~3.25 (m, 2H, -$CH_2$-), 3.34~3.64 (m, 2H, N-$CH_2$-) 4.36 (s, 2H), 7.04~7.32 (m, 4H, phenyl)

REFERENCE EXAMPLE 8

Synthesis of 1-aminoimidazole p-toluenesulfonic acid

In 50 ml of water was dissolved 2.76 g (20 mmol) of potassium carbonate and 1.36 g (20 mmol) of imidazole was added thereto. 2.26 g (20 mmol) of hydroxylamine-O-sulfonic acid was added thereto and the mixture was stirred at room temperature for 6 hours. The resulting precipitate was filtered off and the filtrate was concentrated under the reduced pressure. To the concentrate were slowly added 10 ml of chloroform and a solution of 3.8 g (20 mmol) of p-toluenesulfonic acid monohydrate in 10 ml of chloroform. Stirring for 30 min, filtration and drying of the mixture gave 1.74 g of the desired compound(34%).

NMR (DMSO-d$_6$, δ) 2.30 (s, 3H, CH$_3$), 7.26 (m, 4H, phenyl) 7.69 (d, 2H), 9.10 (t, 1H)

REFERENCE EXAMPLE 9

Synthesis of 1-aminopyrazole p-toluenesulfonic acid

In 500 ml of water were dissolved 2.76 g(20 mmol) of potassium carbonate and 1.31 g(20 mmol) of pyrazole and 2.26 g(20 mmol) of hydroxylamine-O-sulfonic acid was added thereto. The reaction mixture was stirred at room temperature for 6 hours and concentrated under the reduced pressure. To the concentrate was added methanol to give precipitate, which was filtered off. After concentrating under the reduced pressure, the concentrate was treated in the same way as Reference Example 8 to give 1.54 g of the desired compound(30%).

NMR (DMSO-d$_6$, δ) 2.32 (s, 3H, CH$_3$), 6.7 (t, 1H) 7.3 (m, 4H, phenyl), 7.65 (d, 2H)

REFERENCE EXAMPLE 10

Synthesis of 1-aminobenzotriazole

In 200 ml of water were dissolved 23.83 g(0.2 mol) of 1H-benzotriazole and 56.11 g(1 mol) of potassium hydroxide and the solution was maintained at 60° C. To the reaction solution was slowly added 45.2 g(0.4 mol) of hydroxylamine-O-sulfonic acid over 1 hour while maintaining the temperature at 70°~75° C. After completion of addition, the reaction mixture was stirred at 70° C. for further 1 hour. After completion of reaction, the reaction solution was cooled to room temperature to precipitate potassium sulfate as crystal, which was filtered off. The filtrate was extracted with dichloromethane (100 ml×5) and the extract was dried over anhydrous magnesium sulfate and concentrated under the reduced pressure to give yellow crystal.

Thus obtained crystal was dissolved in 5 ml of tetrahydrofuran and the pH was adjusted to 1 with conc.hydrochloric acid to give white crystal.

The filtered crystal was dissolved in 50 ml of water and the pH was adjusted to 11~12 with 30% sodium hydroxide followed by extraction with dichloromethane(30 ml×4). The extract was dried over anhydrous magnesium sulfate and concentrated under the reduced pressure to give 12.07 g of the desired compound(45%).
m.p.=83°~84° C.

NMR (CDCl$_3$, δ) 5.80 (br, 2H, NH$_2$), 7.25~7.55 (m, 2H) 7.70~8.11 (m, 2H)

REFERENCE EXAMPLE 11

Synthesis of 1-amino-1,2,4-triazole

In 20 ml of ethanol was dissolved 14.03 g(250 mmol) of potassium hydroxide and 3.45 g(50 mmol) of 1,2,4-triazole was added thereto. The solution of 11.31 g(100 mmol) of hydroxylamine-O-sulfonic acid in a mixed solvent of water(10 ml) and ethanol(10 ml) was slowly added to the mixture over 30 min. After stirring at room temperature for 2.5 hours, the resulting precipitate was filtered off and the filtrate was concentrated. To the concentrate was added tetrahydrofuran and the mixture was stirred for 30 min.

The tetrahydrofuran layer was separated, concentrated under the reduced pressure and diethyl ether was added thereto. The mixture was stirred for 30 min and the diethyl ether layer was separated and concentrated under the reduced pressure. Crystallization of the concentrate from diisopropyl ether/n-hexane gave the 1.63 g of the desired compound in a form of crystal (46%).
m.p. =48°~50° C.

NMR (DMSO-d$_6$+D$_2$O, δ) 8.58 (s, 1H), 9.36(s, 1H)

REFERENCE EXAMPLE 12

Synthesis of 1-aminoindazole

To a solution of 2.2 g(55 mmol) of sodium hydroxide in 30 ml of water was added 1.33 g(10 mmol) of 1H-indazole and ethanol was slowly added at 50° C. until the reaction mixture was dissolved thoroughly. The resulting mixture was heated to 55° C. and 2.83 g(25 mmol) of hydroxylamine-O-sulfonic acid was slowly added over 30 min with vigorous stirring followed by further stirring for 30 min. After completion of reaction, the resulting precipitate was filtered off, and the filtrate was extracted with dichloromethane(30 ml×2), dried over anhydrous magnesium sulfate and concetrated under the reduced pressure. The concentrate was chromatographed over silica gel using 10% ethyl acetate/dichloromethane as an eluent. The fractions containing the desired product were concentrated under the reduced pressure and crystallized from benzene/petroleum ether to give 0.63 g of the desired compound(47%).
m.p. =104°~106° C.

NMR (DMSO-d$_6$, δ) 5.41 (s, 2H, NH$_2$), 6.85~7.95 (m, 4H) 8.05 (s,1H)

REFERENCE EXAMPLE 13

Synthesis of 1-aminotetrazole

In 125 ml of water was dissolved 13.8 g(100 mmol) of potassium carbonate and 7 g(100 mmol) of 1H-tetrazole was added thereto. The reaction solution was heated to 75° C. and 11.3 g(100 mmol) of hydroxylamine-O-sulfonic acid was slowly added at 70°~75° C. over 30 min while adjusting its pH to 7~8. After completion of addition, the solution was refluxed for 30~35 min, the pH was adjusted to 8 and the solution was extracted with ethyl acetate. The extract was concentrated under the reduced pressure to give 1.7 g of the desired compound(20%).
b.p. =153°~158° C.(2mmHg)

NMR (DMSO-d$_6$, δ) 7.10 (br, 2H, NH$_2$), 9.12 (s, 1H)

REFERENCE EXAMPLE 14

Synthesis of 1-amino-1,2,3-triazole

In 20 ml of distilled water were dissolved 2.76 g(20 mmol) of potassium carbonate and 1.38 g(20 mmol) of 1H-1,2,3-triazole and 2.26 g(20 mmol) of hydroxylamine-O-sulfonic acid was added thereto. The mixture was stirred at room temperature for 9 hours, concentrated under the reduced pressure and ethanol was added to give a precipitate, which was filtered off. The filtrate was concentrated under the reduced pressure and crystallized from tetrahydrofuran/diethyl ether/chloroform to give 0.96 g of the desired product(57%).
m.p. =51° C.

NMR (DMSO-d$_6$+D$_2$O, δ)

REFERENCE EXAMPLE 15

Synthesis of 1-aminobenzimidazole

In a mixed slovent of water(50 ml) and ethanol(50 ml) was dissolved 19.64 g(35 mmol) of potassium hydroxide and 5.91 g(5 mmol) of 1H-benzimidazole was added thereto. Water(10 ml) containing 14.41 g (125 mmol) of hydroxylamine-O-sulfonic acid was slowly added while maintaining the temperature at 30° C. and the mixture was stirred at the same temperature for 18 hours.

The insoluble was filtered off, and the filtrate was extracted with ethyl acetate. The ethyl acetate layer was dried over anhydrous magnesium sulfate and concentrated to driness. The concentrate was subjected to column chromatography over silica gel using 50% ethyl acetate/dichloromethane as an eluent. The fractions containing the desired product were concentrated under the reduced pressure to give 3.06 g of the desired compound in a form of white crystal(46%).

m.p.=141° C.

NMR (DMSO-d$_6$, δ) 6.19 (br, 2H, NH$_2$), 7.08~7.44 (m, 2H) 7.45~7.76 (m, 2H), 8.13 (s, 1H)

REFERENCE EXAMPLE 16

Synthesis of 1-amino-1,4,5,6-tetrahydropyrimidine

To 2.76 g(20 mmol) of potassium carbonate were added 30 ml of water and 10 ml of ethanol, and 1.64 ml(20 mmol) of 1H-1,4,5,6-tetrahydropyrimidine was added thereto. Water(10 ml) containing 2.26 g(20 mmol) of hydroxylamine-O-sulfonic acid was slowly added to the mixture at 30° C. or below and the resulting mixture was stirred at room temperature for 24 hours. After completion of the reaction, the insoluble was filtered off, and the filtrate was extracted twice with ethyl acetate. The ethyl acetate layer containing the desired product was dried over anhydrous magnesium sulfate, concentrated under the reduced pressure and purified by silica gel column chromatography (eluent: 10% aqueous methanol) to give 0.56 g of the desired compound(28%).

NMR (DMSO-d$_6$, δ) 1.4~1.8 (q, 2H), 3.3~3.8 (m, 4H) 3.6 (s, 1H), 6.5 (br, 2H)

REFERENCE EXAMPLE 17

Synthesis of 1-amino-1-methyl piperazinium chloride hydrochloride

In 30 ml of water was dissolved 2.84 g(20 mmol) of 4-acetyl-1-methyl piperazine and 3.4 g(30 mmol) of hydroxylamine-O-sulfonic acid was added thereto. To the mixture, 2.4 g(60 mmol) of sodium hydroxide was added in small amounts and the resulting mixture was stirred at 40° C. for 2 hours, cooled to 5° C. and the pH was adjusted to 7~8 with conc.hydrochloric acid while keeping the above temperature. The reaction solution was concentrated under the reduced pressure to remove water and methanol was added to the residue. The mixture was stirred for 1 hour and filtered. The filtrate was dried over anhydrous magnesium sulfate and concentrated under the reduced pressure to give 2.8 g of 1-methyl-1-amino-4-acetylpiperazinium in a form of white crystal(88.5%).

Thus obtained product 2.8 g(18 mmol) was dissolved in 50 ml of water and 2.88 g(72 mmol) of sodium hydroxide was added thereto. The reaction mixture was stirred at 50° C. for 2 hours and the pH was adjusted to 1 with conc.hydrochloric acid. The mixture was concentrated under the reduced pressure and methanol was added thereto. The resulting mixture was stirred for 1 hour and the precipitate was filtered off. The methanol solution containing the desired product was dried over anhydrous magnesium sulfate and concentrated under the reduced pressure to give 2.33 g of the desired compound in a form of white crystal (62%).

m.p.=230° C. (dec.)

NMR (DMSO-d$_6$, δ) 3.98~3.65 (m, 4H, —CH$_2$—NH—CH$_2$), 3.53 (s, 3H, CH$_3$) 3.75~4.10 (m, 4H), 6.57 (s, 2H, NH$_2$)

EXAMPLE 1

Synthesis of (6R,7R)-7-[(Z)-2-(2-aminothiazol-4-yl)-2-methoxyiminoacetamido]-3-(1-aminopyrrolidiniummethyl)-ceph-3-em-4-carboxylate In 40 ml of water was dissolved 8.99 g(60 mmol) of sodium iodide and the solution was heated to 65°~70° C. Sodium (6R,7R)-7-[(Z)-2-(2-aminothiazol-4-yl)-2-methoxyiminoacetamido]-3-acetoxymethyl-ceph-3-em-4-carboxylate(9.54 g,20 mmol) and 2.94 g(24 mmol) of 1-aminopyrrolidine hydrochloride were added thereto and the mixture was stirred for 1.5 hours while adjusting its pH to 6~6.5. The reaction solution was cooled to room temperature, its pH was adjusted to 1~1.5 with 3N hydrochloric acid and then was stirred for 30 min. The resulting precipitate was filtered off and the filtrate was concentrated under the reduced pressure and a small amount of water was added thereto. Column chromatography over aluminium oxide (80% aqueous acetonitrile), silica gel (80% aqueous acetonitrile) and then DIAION® HP-20(Mitsubishi)(80% aqueous acetonitrile) were conducted. Concentration followed by lyophilization gave 2.12 g of the desired product in a form of white power(22%).

Rf=0.31 (in 80% aqueous acetonitrile)
m.p.=182° C.~(decomp.)
MS (FAB, M+1)=482
NMR (20% DCl, δ) 1.75~2.30 (m, 4H), 2.90~3.70 (m, 6H) 3.80 (s, 3H, OCH$_3$), 3.80~4.20 (m, 1H, C-3) 4.4~4.9 (m, 1H, C-3), 5.17 (dd, 1H, C-6) 5.7 (dd, 1H, C-7), 7.15 (s, 1H, thiazole-H)

EXAMPLE 2

Synthesis of (6R,7R)-[(Z)-2-(2-aminothiazol-4-yl)-2-methoxyiminoacetamido]-3-[(4-aminomorpholin-4-ium)methyl]-ceph-3-em-4-carboxylate By following the procedure in Example 1 except that 2.3 ml (24 mmol) of 4-aminomorpholine was employed in place of 1-aminopyrrolidine, there was obtained 2.5 g of the desired compound (25%).

Rf=0.35 (in 80% aqueous acetonitrile)
m.p.=126° C.~(decomp.)
NMR (20% DCl, δ) 3.35~4.55 (m, 10H, morpholine, C-2), 4.09 (s, 3H, OCH$_3$) 4.95~5.34 (q, 2H, C-3), 5.32 (d, 1H, C-6) 5.85 (d, 1H, C-7), 7.20 (s, 1H, thiazole-H)

EXAMPLE 3

Synthesis of (6R,7R)-7-[(Z)-2-(2-aminothiazol-4-yl)-2-methoxyiminoacetamido]-3-(1-aminopiperidiniummethyl)ceph-3-em-4-carboxylate By following the procedure in Example 1 except that 2.59 ml (24 mmol) of 1-aminopiperidine was employed in place of 1-aminopyrrolidine, there was obtained 2.3 g of the desired product(23%).

Rf=0.35 (in 80% aqueous acetonitrile)

m.p.=120° C. ~(decomp.)

NMR (20% DCl, δ) 1.5~2.2 (m, 6H), 3.75 (s, 3H, OCH$_3$), 3.2~4.35 (m, 6H) 4.89~5.2 (m, 2H, C-3), 5.37 (d, 1H, C-6) 5.95(d, 1H, C-7), 7.18 (s, 1H, thiazole-H)

EXAMPLE 4

Synthesis of (6R,7R)-7-[(Z)-2-(2-aminothiazol-4-yl)-2-methoxyiminoacetamido]-3-[(1-amino-4-hydroxypiperidinium)methyl]-ceph-3-em-4-carboxylate By following the procedure in Example 1 except that 2.79 g (24 mmol) of 1-amino-4-hydroxypiperidine was employed in place of 1-aminopyrrolidine, there was obtained 2.1 g of the desired product(20%).

Rf=0.15 (in 80% aqueous acetonitrile)

NMR (20% DCl, δ) 1.12~1.98 (m, 4H), 3.2~4.4 (m, 7H) 3.85 (s, 3H, OCH$_3$), 4.86~5.2 (br, 2H, C-3) 5.34(d, 1H, C-6), 5.96 (d, 1H, C-7) 7.2 (s, 1H, thiazole-H)

EXAMPLE 5

Synthesis of (6R,7R)-7-[(Z)-2-(2-aminothiazol-4-yl)-2-methoxyiminoacetamido]-3-[(2-amino-1,2,3,4-tetrahydroisoquinolin-2-ium)methyl]-ceph-3-em-4-carboxylate In a mixed solvent of acetonitrile(5 ml) and water(30 ml) was dissolved 4.02 g(30 mmol) of lithium iodide, 0.99 g(6.68 mmol) of 2-amino-1,2,3,4-tetrahydroisoquinoline was added thereto and the temperature was raised to 67°~70° C. To the reaction solution was added 1.43 g(3 mmol) of sodium(6R,7R)-7-[(Z)-2-(2-aminothiazol-4-yl)-2-methoxyiminoacetamido]-3-acetoxymethyl-ceph-3-em-4-carboxylate, and the reaction mixture was stirred at 70°~72° C. for 2 hours while adjusting the pH to 6.5~7.0.

After completion of reaction, the reaction solution was cooled to room temperature and stirred for 30 min while adjusting the pH to 1~1.5 with 1N hydrochloric acid. The insoluble was filtered off and the filtrate was concentrated under the reduced pressure. The concentrate was subjected to column chromatography over aluminium oxide and silica gel(eluent: 80% aqueous acetonitrile). The fractions obtained were concentrated under the reduced pressure, and the concentrate was dissolved in a small amount of water followed by purification by DIAION® HP-20(Mitsubishi) chromatography(eluent: 8% aqueous ethanol).

The fractions containing the desired product were concentrated under the reduced pressure and freeze-dried to give 0.23 g of the desired compound in a pale yellow amorphous form(14%).

Rf=0.4 (in 80% aqueous acetonitrile)

MS(FAB, M+1)=544

NMR (DMSO-d$_6$+20% DCl, δ) 3.1~3.5 (m, 2H), 3.5~4.3 (m, 6H) 4.04 (s, 3H, OCH$_3$), 4.5~5.1 (m, 2H, C-3) 5.2 (dd, 1H, C-6), 5.8 (dd, 1H, C-7) 7.09 (s, 1H, thiazole-H), 7.1~7.8 (m, 4H, phenyl)

EXAMPLE 6

Synthesis of (6R, 7R)-7-[(Z)-2-(2-aminothiazol-4-yl)-2-methoxyiminoacetamido]-3-(1-aminoindoliniummethyl)-ceph-3-em-4-carboxylate By following the procedure in Example 5 except that 0.9 g (6.68 mmol) of 1-aminoindoline was employed in place of 2-amino-1,2,3,4-tetrahydroisoquinoline, there was obtained 0.2 g of the desired product (13%).

Rf=0.37 (in 80% aqueous acetonitrile)

NMR (DMSO-d$_6$+20% DCl, δ) 2.8~3.1 (m, 2H), 3.4~4.4 (m, 4H) 4.01 (s, 3H, OCH$_3$), 4.6~5.1 (m, 2H, C-3) 5.1 (d, 1H, C-6), 5.7 (d, 1H, C-7) 7.01 (s, 1H, thiazole-H), 7.03~7.7 (m, 4H, phenyl)

EXAMPLE 7

Synthesis of (6R, 7R)-7-[(Z)-2-(2-aminothiazol-4-yl)-2-methoxyiminoacetamido]-3-(1-aminoindoliummethyl)ceph-3-em-4-carboxylate By following the procedure in Example 5 except that 0.9 g (6.68 mmol) of 1-aminoindole was employed in place of 2-amino-1,2,3,4-tetrahydroisoquinoline, there was obtained 0.26 g of the desired product (17%).

Rf=0.36 (in 80% aqueous acetonitrile)

NMR (DMSO-d$_6$+20% DCl, δ) 3.5~3.9 (m, 2H, C-2), 3.86 (s, OCH$_3$) 4.6~5.1 (m, 2H, C-3), 5.2 (d, 1H, C-6) 5.6 (d, 1H, C-7), 6.45 (d, 1H), 7.01 (s, 1H, thiazole-H) 7.05~7.8 (m, 5H, phenyl)

EXAMPLE 8

Synthesis of (6R, 7R)-7-[(Z)-2-(2-aminothiazol-4-yl)-2-methoxyiminoacetamido]-3-[(1-amino-1,2,3,6-tetrahydropyridinium) methyl]-ceph-3-em-4-carboxylate In a mixed solvent of acetonitrile (4 ml) and water (9 ml) was dissolved 3.21 g (24 mmol) of lithium iodide and the solution was heated to 70° C. 0.33 g (3.36 mmol) of 1-amino-1,2,3,6-tetrahydropyridine was added thereto and 0.764 g (1.6 mmol) of sodium (6R, 7R)-7-[(Z)-2-(2-aminothiazol-4-yl)methoxyiminoacetamido]-3-acetoxymethyl-ceph-3-em-4-carboxylate was added while adjusting the pH to 6.5~7. The mixture was stirred at 70°~72° C. for 1 hour while adjusting the pH to 6.5~7.0.

The reaction solution was cooled to room temperature, and its pH was adjusted to 1~1.5 with 3N hydrochloric acid. The solution was stirred for 30 min, the resulting precipitate was filtered off and the filtrate was concentrated under the reduced pressure. The concentrate was dissolved in a small amount of water and subjected to column chromatography over aluminium oxide (80% aqueous acetonitrile), silica gel (85% aqueous acetonitrile) and DIAION® HP-20 (Mitsubishi) (80% aqueous acetonitrile). The fractions containing the desired product were concentrated and freeze-dried to give 158 mg of the desired compound (20%).

Rf=0.29 (in 80% aqueous acetonitrile)

NMR (DMSO-d$_6$, δ) 2.0~2.4 (m, 2H), 3.0~3.9 (m, 6H) 3.97 (s, 3H, OCH$_3$), 4.0~4.3 (m, 1H, C-3) 4.7~5.1 (m, 1H, C-3), 5.15 (d, 1H, C-6) 5.5~5.9 (m, 3H, C-7), 6.73 (s, 1H, thiazole-H) 9.5 (d, 1H, -NH)

EXAMPLE 9

Synthesis of (6R, 7R)-7-[(Z)-2-(2-aminothiazol-4-yl)-2-methoxyiminoacetamido]-3-[(1-amino-3-pyrrolin-1-ium)methyl]-ceph-3-em-4-carboxylate By following the procedure in Example 8 except that 0.28 g (3.36 mmol) of 1-amino-3-pyrroline was employed in place of 1-amino-1,2,3-6-tetrahydropyridine, there was obtained 0.17 g of the desired compound (22%).

Rf=0.3 (in 80% aqueous acetonitrile)
NMR (DMSO-d$_6$+20% DCl, δ) 3.6~4.0 (m, 2H, C-2), 3.86 (s, 3H, OCH$_3$) 4.6 (s, 4H), 4.56~5.1 (m, 2H, C-3) 5.2(d, 1H, C-6), 5.6 (d, 1H, C-7) 5.9 (s, 2H), 7.01 (s, 1H, thiazole-H)

EXAMPLE 10

Synthesis of (6R, 7R)-7-[(Z)-2-(2-aminothiazol-4-yl)-2-methoxyiminoacetamido]-3-(1-aminopyrroliummethyl)ceph-3-em-4-carboxylate By following the procedure in Example 8 except that 0.28 g (3.36 mmol) of 1-aminopyrrole was employed in place of 1-amino-1,2,3,6-tetrahydropyridine, there was obtained 0.16 g of the desired compound (21%).

Rf=0.29 (in 80% aqueous acetonitrile)
NMR (DMSO-d$_6$+20% DCl, δ) 3.6~4.1 (m, 2H, C-2), 3.83 (s, 3H, OCH$_3$) 4.6~5.1 (m, 2H, C-3), 5.15 (d, 1H, C-6) 5.62(d, 1H, C-7), 6.1 (t, 2H) 6.5 (t, 2H), 7.01 (s, 1H, thiazole-H)

EXAMPLE 11

Synthesis of (6R, 7R)-7-[(Z)-2-(2-aminothiazol-4-yl)-2-methoxyiminoacetamido]-3-[(1-amino-1-methyl-4-piperazinium)methyl]ceph-3-em-4-carboxylate In 8 ml of water was dissolved 2.5 g (17 mmol) of sodium iodide, 8 ml of acetonitrile was added thereto and the mixture was heated to 65°~70° C. 0.376 g(2 mmol) of 1-amino-1-methylpiperazinium chloride hydrochloride and 0.48 g (1 mmol) of sodium (6R, 7R)-7-[(Z)-2-(2-aminothiazol-4-yl)-2-methoxyiminoacetamido]-3-acetoxymethyl-ceph-3-em-4-carboxylate were added in this order and the pH was adjusted to 6.8 with sodium bicarbonate solution. The reaction solution was stirred at 65°~70° C. for 2 hours, cooled to room temperature and washed three times with 50 ml of dichloromethane. The aqueous layer was adjusted to pH 2 with 6N hydrochloric acid, concentrated under the reduced pressure and the resulting precipitate was filtered off. The filtrate was concentrated under the reduced pressure and the concentrate was subjected to silica gel column chromatography (80% aqueous acetonitrile). The fractions containing the desired product were purified by HP-20 column chromatography using the same eluent to give 0.37 g of the desired compound(73%).

Rf=0.11 (in 80% aqueous acetonitrile)
m.p. =194° C.~(decomp.)
MS(FAB, M+1)=511
NMR (DMSO-d$_6$, δ) 3.0~3.7 (m, 15H), 3.83 (s, 3H, OCH$_3$) 4.96 (d, 1H, C-6), 5.51 (dd, 1H, C-7) 6.03(s, 2H, NH$_2$), 6.73 (s, 1H, thiazole-H) 7.18 (br, 2H), 9.45 (d, 1H, -NH)

EXAMPLE 12

Synthesis of (6R, 7R)-7-[(Z)-2-(2-aminothiazol-4-yl)-2-methoxyiminoacetamido]-3-[(4-amino-1,2,4-triazol-2-ium)methyl]-ceph-3-em-4-carboxylate In 25 ml of distilled water was dissolved 4.3g (30 mmol) of sodium iodide and the solution was heated to 70°~75° C. 1.0 g(12 mmol) of 4-amino-1,2,4-triazole and 4.77 g(10 mmol) of sodium (6R, 7R)-7-[(Z)-2-(2-aminothiazol-4-yl)-2-methoxyiminoacetamido]-3-acetoxymethyl-ceph-3-em-4-carboxylate were added thereto and the pH was adjusted to 6~6.5. The reaction mixture was stirred at 70°~75° C. for 1 hour, the reaction solution was cooled to room temperature and the pH was adjusted to 1~1.5 with 3N hydrochloric acid. The resulting precipitate was filtered off and the filtrate was concentrated under the reduced pressure. The concentrate was dissolved in a small amount of water and subjected to column chromatography over aluminum oxide (80% aqueous acetonitrile) and HP-20 (85% aqueous acetonitrile). The fractions containing the desired product were concentrated and freeze-dried to give 1.68 g of the desired product(35%).

Rf=0.23 (in 80% aqueous acetonitrile)
m.p. = 170° C. ~ (decomp.)
MS(FAB, M+1)=480
NMR (DMSO-d$_6$+20% DCl, δ) 3.3~3.6 (m, 2H, C-2), 3.83 (s, 3H, OCH$_3$) 5.04 (d, 1H, C-6), 5.0~5.35 (q, 2H, C-3) 5.6(d, 1H, C-7), 7.01 (s, 1H, thiazole-H) 8.76, 9.81 (s,s, 2H, triazole)

EXAMPLE 13

Synthesis of (6R,7R)-7-[(Z)-2-(2-aminothiazol-4-yl)-2-methoxyiminoacetamido]-3-[(1-amino-1,2,4-triazol-4-ium)-methyl-]-ceph-3-em-4-carboxylate In a mixed solvent of acetonitrile (10 ml) and water(10 ml) was dissolved 9.69 g(64.65 mmol) of sodium iodide and the solution was heated to 70°~75° C. 1.63 g(19.4 mmol) of 1-amino-1,2,4-triazole and 6.17 g(12.93 mmol) of sodium (6R,7R)-7-[(Z)-2-(2-aminothiazol-4-yl)-2-methoxyiminoacetamido]-3-acetoxymethyl-ceph-3-em-4-carboxylate were added thereto, and the mixture was stirred at 70°~75° C. for 1.5 hours while adjusting the pH to 6~6.5 and cooled to room temperature. After adjusting the pH to 1~1.5 with 3N hydrochloric acid, the reaction mixture was stirred for 30 min. The resulting precipitate was filtered off and the filtrate was concentrated under the reduced pressure. The concentrate was dissolved in a small amount of water and subjected to column chromatography over aluminium oxide (80% aqueous acetonitrile), silica gel (85% aqueous acetonitrile) and then HP-20 (Mitsubishi) (80% aqueous acetonitrile). The fractions containing the desired product were concentrated and freeze-dried to give 2.05 g of the desired compound (33%).

Rf=0.31 (in 80% aqueous acetonitrile)
m.p. = 166° C. ~ (decomp.)
MS(FAB, M+1)=480
NMR (DMSO-d$_6$+20% DCl, δ) 3.28~3.7 (m, 2H, C-2), 3.83 (s, 3H, OCH$_3$) 5.1 (q, 2H, C-3), 5.18 (d, 1H, C-6) 5.61 (d, 1H, C-7), 6.91 (s, 1H, thiazole-H) 8.74, 9.68 (s,s, 2H, triazole)

EXAMPLE 14

Synthesis of (6R, 7R)-7-[(Z)-2-(2-aminothiazol-4-yl)-2-methoxyiminoacetamido]-3-[(1-aminoimidazol-3-ium)methyl]-ceph-3-em-4-carboxylate By following the procedure in Example 13 except that 1.61 g(19.4 mmol) of 1-aminoimidazole was employed in place of 1-amino-1,2,4-triazole, there was obtained 1.95 g of the desired compound (32%).

Rf=0.29 (in 80% aqueous acetonitrile)
NMR (DMSO-d$_6$+20% DCl, δ) 3.2~3.74 (m, 2H, C-2), 3.86 (s, 3H, OCH$_3$) 5.08 (q, 2H, C-3), 5.2 (d, 1H, C-6) 5.6 (d, 1H, C-7), 6.95 (s, 1H, thiazole-H) 7.6, 8.3 (s,s, 2H), 9.3 (s, 1H)

EXAMPLE 15

Synthesis of (6R, 7R)-7-[(Z)-2-(2-aminothiazol-4-yl)-2-methoxyiminoacetamido]-3-[(1-aminopyrazol-2-ium)methyl]-ceph-3-em-4-carboxylate By following the procedure in Example 13 except that 1.61 g (19.4 mmol) of 1-aminopyrazole was employed in place of 1-amino-1,2,4-triazole, there was obtained 1.81 g of the desired compound (29%).

Rf=0.3 (in 80% aqueous acetonitrile)
NMR (DMSO-$d_6$+20% DCl, $\delta$) 3.27~3.74 (m, 2H, C-2), 3.9 (s, 3H, OCH$_3$) 5.1 (q, 2H, C-3), 5.15 (d, 1H, C-6) 5.68 (d, 1H, C-7), 6.7 (t, 1H) 7.02 (s, 1H, thiazole), 7.8, 8.4 (s,s 2H)

EXAMPLE 16

Synthesis of (6R, 7R)-7-[(Z)-2-(2-aminothiazol-4-yl)-2-methoxyiminoacetamido]-3-[(1-aminotetrazol-4-ium)methyl]-ceph-3-em-4-carboxylate By following the procedure in Example 13 except that 1.67 g (19.4 mmol) of 1-aminotetrazole was employed in place of 1-amino-1,2,4-triazole, there was obtained 1.73 g of the desired compound (28%).

Rf=0.25 (in 80% aqueous acetonitrile)
NMR (DMSO-$d_6$+20% DCl, $\delta$) 3.20~3.74 (m, 2H, C-2), 3.83 (s, 3H, OCH$_3$) 5.12 (q, 2H, C-3), 5.21 (d, 1H, C-6) 5.63(d, 1H, C-7), 7.01 (s, 1H, thiazole-H) 9.7 (s, 1H, tetrazole)

EXAMPLE 17

Synthesis of (6R,7R)-7-[(Z)-2-(2-aminothiazol-4-yl)-2-methoxyiminoacetamido]-3-[(1-amino-1,2,3-triazol-3-ium)methyl]-ceph-3-em-4-carboxylate By following the procedure in Example 13 except that 1.63 g(19.4 mmol) of 1-amino-1,2,3-triazole was employed in place of 1-amino-1,2,4-triazole, there was obtained 2.02 g of the desired compound(33%).

Rf=0.24 (in 80% aqueous acetonitrile)
m.p.=126° C.~(decomp.)
MS(FAB, M+1)=480
NMR (DMSO-$d_6$+20% DCl, $\delta$) 3.21~3.68 (m, 2H, C-2), 3.9(s, 3H, OCH$_3$) 5.12 (q, 2H, C-3), 5.16 (d, 1H, C-6) 5.65(d, 1H, C-7), 7.01 (s, 1H, thiazole-H) 7.8, 8.7 (s,s, 2H, triazole)

EXAMPLE 18

Synthesis of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate In a mixed solvent of acetonitrile(10 ml) and water(15 ml) was dissolved 6.69 g(50 mmol) of lithium iodide and the solution was heated to 65°~67° C. 2.42 g(18 mmol) of 1-aminobenzotriazole and 4.77 g(10 mmol) of sodium (6R,7R)-7-[(Z)-2-(2-aminothiazol-4-yl)-2-methoxyiminoacetamido]-3-acetoxymethyl-ceph-3-em-4-carboxylate were added thereto, and the mixture was stirred at 72° C. for 1 hour while adjusting the pH to 6.5~7.0.

After completion of reaction, the reaction solution was cooled to room temperature and stirred for 30 min while adjusting its pH to 1~1.5 with 3N hydrochloric acid. The insoluble was filtered off and the filtrate was concentrated under the reduced pressure. The concentrate was subjected to column chromatography over aluminium oxide and silica gel using 80% aqueous acetonitrile as an eluent. The fractions obtained were concentrated under the reduced pressure and dissolved in a small amount of water. This was purified by HP-20(Mitsubishi) column chromatography (eluent: 15% aqueous acetonitrile). The fractions containing the desired product were concentrated under the reduced pressure and freeze-dried to give 1.48 g of the desired compound in pale yellowish white amorphous form (28%).

Rf=0.3 (in 80% aqueous acetonitrile)
m.p.=168° C.~(decomp.)
MS(FAB, M+1)=530
NMR (DMSO-$d_6$+20% DCl, $\delta$) 3.85~4.0 (m, 2H, C-2), 4.05(s, 3H, OCH$_3$) 5.05~5.5(q, 2H, C-3), 5.3 (d, 1H, C-6) 5.86(d, 1H, C-7), 7.04 (s, 1H, thiazole-H) 7.65~8.1 (m, 4H, phenyl)

EXAMPLE 19

Synthesis of (6R,7R)-7-[(Z)-2-(2-aminothiazol-4-yl)-2-methoxyiminoacetamido]-3-[(1-aminobenzimidazol-3-ium)methyl]-ceph-3-em-4-carboxylate In a mixed solvent of acetonitrile(10 ml) ad water(20 ml) was dissolved 16.06 g(120 mmol) of lithium iodide, the solution was heated to 65° C. and 3.2 g(24 mmol) of 1-aminobenzimidazole and 5.73 g(12 mmol) of sodium (6R,7R)-7-[(Z)-2-(2-aminothiazol-4-yl)-2-methoxyiminoacet-amido]-3-acetoxymethyl-ceph-3-em-4-carboxylate were added thereto. The reaction mixture was stirred at 70° C. for 1.5 hours while adjusting the pH to 6.5~7.0.

After completion of reaction, the reaction solution was cooled to room temperature and the pH was adjusted to 1~1.5 with 3N hydrochloric acid. The insoluble was filtered off and the filtrate was concentrated under the reduced pressure. The concentrate was subjected to column chromatography over aluminium oxide and then silica gel (eluent: 80% aqueous acetonitrile). The fraction obtained were concentrated under the reduced pressure and dissolved in a small amount of water. This was purified by HP-20 (Mitsubishi) column chromatography using 15% aqueous acetonitrile. The fractions containing the desired product were concentrated under the reduced pressure and freeze-dried to give 2.28 g of the desired compound in a white amorphous form(36%).

Rf=0.3 (in 80% aqueous acetonitrile)
m.p.=155° C.~(decomp.)
MS(FAB, M+1)=529
NMR (DMSO-$d_6$, $\delta$) 3.2~3.7 (m, 2H, C-2), 3.8 (s, 3H, OCH$_3$) 5.04 (d, 1H, C-6), 5.4~5.8 (m, 3H, C-3, C-7) 6.75 (s, 1H, thiazole-H), 7.5~8.5 (m, 4H, phenyl) 10.15 (s, 1H, imidazole)

EXAMPLE 20

Synthesis of (6R,7R)-7-[(Z)-2-(2-aminothiazol-4-yl)-2-methoxyiminoacetamido]-3-[(1-aminoindazol-2-ium)methyl]-ceph-3-em-4-carboxylate By following the procedure in Example 19 except that 3.2 g(24 mmol) of 1-aminoindazole was employed in place of 1-aminobenzimidazole, there was obtained 1.94 g of the desired compound(31%).

Rf=0.31 (in 80% aqueous acetonitrile)

NMR (DMSO-d$_6$+20% DCl, δ) 3.87~4.1 (m, 2H, C-2), 4.02 (s, 3H, OCH$_3$) 5.3 (q, 2H, C-3), 5.33 (d, 1H, C-6) 5.82 (d, 1H, C-7), 7.03 (s, 1H, thiazole-H) 7.1~8.2 (m, 4H, phenyl), 8.8 (s, 1H)

EXAMPLE 21

Synthesis of (6R,7R)-7-[(Z)-2-(2-aminothiazol-4-yl)-2-methoxyiminoacetamido]-3-[(1-amino-1,4,5,6-tetrahydropyrimidin-3-ium)methyl]-ceph-3-em-4-carboxylate By following the procedure in Example 19 except that 2.38 g(24 mmol) of 1-amino-1,4,5,6-tetrahydropyrimidine was employed in place of 1-aminobenzimidazole, there was obtained 1.68 g of the desired compound (28%).

Rf=0.29 (in 80% aqueous acetonitrile)

NMR (DMSO-d$_6$+20% DCl, δ) 1.4~1.8 (q, 2H), 3.3~3.9 (m, 6H) 3.98 (s, 3H, OCH$_3$), 5.21 (q, 2H, C-3) 5.3 (d, 1H, C-6), 5.75 (d, 1H, C-7) 7.04 (s, 1H, thiazole-H), 8.5 (s, 1H)

PREPARATION EXAMPLE 1

Synthesis of (6R,7R)-7-[(Z)-2-(2-aminothiazol-4-yl)-2-carboxymethoxyiminoacetamido]-3-acetoxymethyl-ceph-3-em-4-carboxylic acid A) In 15 ml of N,N-dimethylformamide were dissolved 1.09 g(2 mmol) of (Z)-2-(2-tritylaminothiazol-4-yl)-2-(2-tert-butoxycarbonylmethoxyimino) acetic acid and 0.88 g(2 mmol) of diphenylmethyl 7β-amino-3-acetoxymethyl-ceph-3-em-4-carboxylate, and the solution was stirred and cooled to 0° C. 0.28 g(2.1 mmol) of 1-hydroxybenzotriazole and then 0.43 g(2.1 mmol) of dicyclohexylcarbodiimide were added thereto. The reaction mixture was stirred at room temperature for 5 hours and left to stand overnight. The reaction mixture was filtered and the filtered solid was washed with diethyl ether. The filtrate and the washing were combined together and 100 ml of water added thereto followed by extraction with ethyl acetate. The organic layer was washed with water, 1N hydrochloric acid, sodium bicarbonate solution and then saturated brine, separated, dried over anhydrous sodium sulfate and concentrated under the reduced pressure. The concentrate was subjected to silica gel chromatography(eluent: 2.5% methanol/dichloromethane). The desired fractions were concentrated under the reduced pressure and crystallized from diisopropylether to give 1.35 g of diphenylmethyl (6R,7R)-7-[(Z)-2-(2-tritylaminothiazol-4-yl)-2-(2-tert-butoxycarbonylmethoxyimino)acetamido]-3-acetoxymethyl-ceph-3-em-4-carboxylate as a desired compound(70%).

B) In a mixed solvent of anisole(15 ml) and trifluoroacetic acid(15 ml) was dissolved 1.35 g(1.4 mmol) of the product prepared in the above(A) at 0° C. and the solution was stirred at room temperature for 2 hours. After completion of the reaction, the reaction solution was concentrated under the reduced pressure and the residue was placed in 150 ml of n-hexane cooled to −20° C.~−30° C. 70 ml of diethyl ether was added thereto and the resulting precipitate was filtered to give 0.75 g of (6R,7R)-7-[(Z)-2-(2-aminothiazol-4-yl)-2-carboxymethoxyiminoacetamido]-3-acetoxymethyl-ceph-3-em-4-carboxylic acid trifluoroacetate. The solid was suspended in 10 ml of water, the pH was adjusted to 6.5 with saturated sodium bicarbonate solution and the solution was washed with ethyl acetate. The aqueous layer was adjusted to pH 1.5 and the resulting precipitate was filtered to give 0.48 g of (6R,7R)-7-[(Z)-2-(2-aminothiazol-4-yl)-2-carboxymethoxyiminoacetamido]-3-acetoxymethyl-ceph-3-em-4-carboxylic acid as a desired compound(68%).

Rf=0.65 (in 80% aqueous acetonitrile)

NMR (DMSO-d$_6$, δ) 2.11 (s, 3H), 3.25~3.82 (q, 2H, C-2) 4.60 (s, 2H), 4.79~4.89 (d, 2H, C-3) 5.19~5.25 (d, 1H, C-6), 5.79~5.85 (dd, 1H, C-7) 6.71 (s, 1H, thiazole-H), 7.27 (br, 2H) 9.47 (d, 1H)

EXAMPLE 22

Synthesis of (6R, 7R)-7-[(Z)-2-(2-aminothiazol-4-yl)-2-carboxymethoxyiminoacetamido]-3-[(1-amino-1,2,3,6-tetrahydropyridinium)methyl]-ceph-3-em-4-carboxylate In 15 ml of water was dissolved 3.75 g (25 mmol) of sodium iodide and the solution was heated to 70°~75° C. To this was added 0.59 g (6 mmol) of 1-amino-1,2,3,6-tetrahydropyridine and 2.5 g (5 mmol) of (6R, 7R)-7-[(Z)-2-(2-aminothiazol-4-yl)-2-carboxymethoxyiminoacetamido]-3-acetoxymethyl-ceph-3-em-4-carboxylic acid prepared in Preparation Example 1 was slowly added while adjusting the pH to 6.5~7.0. The mixture was stirred at 70°~75° C. for 2 hours, cooled to room temperature and the pH was adjusted to 1~1.5 with 3N hydrochloric acid. After stirring for 30 min, the resulting precipitate was filtered off and the filtrate was concentrated under the reduced pressure. A small amount of water was added to the concentrate and chromatography over HP-20(eluent: 80% aqueous acetonitrile) was carried out. The fractions containing desired product were concentrated under the reduced pressure and freeze-dried to give 0.46 g of the desired compound (17%).

Rf=0.28 (in 80% aqueous acetonitrile)

NMR (DMSO-d$_6$, δ) 2.1~2.45 (m, 2H), 3.2~4.4 (m, 6H) 4.71 (s, 2H), 4.8~5.2 (m, 2H, C-2) 5.21 (d, 1H, C-6), 5.5~5.87 (m, 3H) 6.72 (s, 1H, thiazole-H), 7.25 (br, 2H) 9.45 (d, 1H, -NH)

EXAMPLE 23

Synthesis of (6R, 7R)-7-[(Z)-2-(2-aminothiazol-4-yl)-2-carboxymethoxyiminoacetamido]-3-(1-aminopiperidininiummethyl)-ceph-3-em-4-carboxylate By following the procedure in Example 22 except that 0.65 ml (6 mmol) of 1-aminopiperidine was employed in place of 1-amino-1,2,3,6-tetrahydropyridine, there was obtained 0.53 g of the desired compound (20%).

Rf=0.33 (in 80% aqueous acetonitrile)

NMR (20% DCl δ) 1.53~2.22 (m, 6H, piperidine) 3.3~4.5 (m, 6H, C-2, piperidine), 4.7 (s, 2H) 4.88~5.21 (m, 2H, C-3), 5.35 (d, 1H, C-6) 5.8 (d, 1H, C-7), 7.2 (s, 1H, thiazole-H)

EXAMPLE 24

Synthesis of (6R, 7R)-7-[(Z)-2-(2-aminothiazol-4-yl)-2-carboxymethoxyiminoacetamido]-3-[(2-amino-1,2,3,4-tetrahydroisoquinolin-2-ium)methyl]-ceph-3-em-4-carboxylate By following the procedure in Example 22 except that 0.89 g (6 mmol) of 2-amino-1,2,3,4-tetrahydroisoquinoline was employed in place of 1-amino-1,2,3,6-tetrahydropyridine, there was obtained 0.55 g of the desired compound (19%).

Rf=0.38 (in 80% aqueous acetonitrile)
NMR (DMSO-d$_6$+20% DCl, δ) 3.1~3.48 (m, 2H), 3.4~4.4 (m, 6H) 4.6~5.0 (m, 2H, C-3), 5.2 (d, 1H, C-6) 5.75 (d, 1H, C-7), 7.05 (s, 1H, thiazole-H) 7.12~7.82 (m, 4H, phenyl)

EXAMPLE 25

Synthesis of (6R, 7R)-7-[(Z)-2-(2-aminothiazol-4-yl)-2-carboxymethoxyiminoacetamidol]-3-[(1-amino-1-methyl-4-piperazinium)methyl]-ceph-3-em-4-carboxylate By following the procedure in Example 22 except that 0.91 g(6 mmol) of 1-amino-1-methyl-4-piperazinium chloride hydrochloride was employed in place of 1-amino-1,2,3,6-tetrahydropyridine, there was obtained 1.25 g of the desired compound (45%).

Rf=0.11 (in 80% aqueous acetonitrile)
NMR (DMSO-d$_6$, δ) 3.0~3.8 (m, 5H), 4.65 (s, 2H) 5.1 (d, 1H, C-6), 5.65 (dd, 1H, C-7) 6.05 (s, 2H, NH$_2$), 6.72 (s, 1H, thiazole-H), 7.2 (br, 2H), 9.3 (d, 1H, -NH)

EXAMPLE 26

Synthesis of (6R,7R)-7-[(Z)-2-(2-aminothiazol-4-yl)-2-carboxymethoxyiminoacetamido]-3-[(4-amino-1,2,4-triazol-2-ium)-methyl]-ceph-3-em-4-carboxylate In 8 ml of water was dissolved 2.25 g (15 mmol) of sodium iodide and the solution was heated to 70°~75° C. 0.3 g(3.6 mmol) of 4-amino-1,2,4-triazole was added and the pH was adjusted to 6.5~7.0. While maintaining the pH at 6.5~7.0, 1.5 g(3 mmol) of (6R,7R)-7-[(Z)-2-(2-aminothiazol-4-yl)-2-carboxymethoxyiminoacetamido]-3-acetoxymethyl-ceph-3-em-4-carboxylic acid prepared in Preparation Example 1 was slowly added. The reaction solution was stirred at 70°~75° C. for 2 hours, cooled to room temperature and the pH was adjusted to 1~1.5 with 3N hydrochloric acid. The solution was stirred for 30 min and the resulting precipitate was filtered off. The filtrate was concentrated, a small amount of water was added and the resulting was subjected to HP-20 chromatography (eluent: 80% aqueous acetonitrile). The fractions containing the desired product were concentrated under the reduced pressure and freeze-dired to give 0.39 g of the desired compound (25%).

Rf=0.23 (in 80% aqueous acetonitrile)
NMR (DMSO-d$_6$+20% DCl, δ) 3.25~3.7 (m, 2H, C-2), 4.7 (s, 2H) 5.04 (d, 1H, C-6), 5.1~5.3 (q, 2H, C-3) 5.65 (d, 1H, C-7), 7.02 (s, 1H, thiazole-H) 8.75, 9.8 (s,s, 2H, triazole)

EXAMPLE 27

Synthesis of (6R,7R)-7-[(Z)-2-(2-aminothiazol-4-yl)-2-carboxymethoxyiminoacetamido]-3-[(1-aminoimidazol-3-ium)methyl]-ceph-3-em-4-carboxylate By following the procedure in Example 26 except that 0.3 g(3.6 mmol) of 1-aminoimidazole was employed in place of 4-amino-1,2,4-triazole, there was obtained 0.31 g of the desired compound(20%).

Rf=0.29 (in 80% aqueous acetonitrile)
NMR (DMSO-d$_6$+20% DCl, δ) 3.28~3.8 (m, 2H, C-2), 4.70 (s, 2H) 5.05 (q, 2H, C-3) 5.22 (d, 1H, C-6) 5.75 (d, 1H, C-7), 7.0 (s, 1H, thiazole-H) 7.6, 8.2 (s,s, 2H, imidazole), 9.0 (s, 1H, imidazole)

EXAMPLE 28

Synthesis of (6R, 7R)-7-[(Z)-2-(2-aminothiazol-4-yl)-2-carboxymethoxyiminoacetamido]-3-[(1-aminopyrazol-2-ium)methyl]-ceph-3-em-4-carboxylate By following the procedure in Example 26 except that 0.3 g(3.6 mmol) of 1-aminopyrazole was employed in place of 4-amino-1,2,4-triazole, there was obtained 0.29 g of the desired compound(18%).

Rf=0.29 (in 80% aqueous acetonitrile)
NMR (DMSO-d$_6$+20% DCl, δ) 3.3~3.75 (m, 2H, C-2), 4.75 (s, 2H) 5.10 (q, 2H, C-3), 5.25 (d, 1H, C-6) 5.7 (d, 1H, C-7), 6.8 (t, 1H, pyrazole) 7.07 (s, 1H, thiazol-H), 7.7, 8.5 (s,s, 2H, pyrazole)

EXAMPLE 29

Synthesis of (6R,7R)-7-[(Z)-2-(2-aminothiazol-4-yl)-2-carboxymethoxyiminoacetamido]-3-[(1-aminoindazol-2-ium)methyl]-ceph-3-em-4-carboxylate By following the procedure in Example 26 except that 0.48 g(3.6 mmol) of 1-aminoindazole was employed in place of 4-amino-1,2,4-triazole, there was obtained 0.32 g of the desired compound(19%).

Rf=0.30 (in 80% aqueous acetonitrile)
NMR (DMSO-d$_6$+20% DCl, δ) 3.85~4.1 (m, 2H, C-2), 4.76 (s, 2H) 5.31 (q, 1H, C-3), 5.4 (d, 1H, C-6) 5.85 (d, 1H, C-7), 7.1 (s, 1H, thiazole-H) 7.2~8.18 (m, 4H, phenyl), 8.5 (s, 1H, indazole)

EXAMPLE 30

Synthesis of (6R,7R)-7-[(Z)-2-(2-aminothiazol-4-yl)-2-carboxymethoxyiminoacetamido]-3-[(1-aminobenzimidazol-3-lum)methyl]-ceph-3-em-4-carboxylate By following the procedure in Example 26 except that 0.48 g(3.6 mmol) of 1-aminobenzimidazole was employed in place of 4-amino-1,2,4-triazole, there was obtained 0.49 g of the desired compound(28%).

Rf=0.3 (in 80% aqueous acetonitrile)
NMR (DMSO-d$_6$+20% DCl, δ) 3.83~4.0 (m, 2H, C-2), 4.7 (s, 2H) 5.06~5.5 (q, 2H, C-3), 5.19 (d, 1H, C-6) 5.79 (d, 1H, C-7), 7.01 (s, 1H, thiazole-H) 7.5~7.9 (m, 4H, phenyl), 9.5 (s, 1H, imidazole)

EXAMPLE 31

Synthesis of (6R,7R)-7-[(Z)-2-(2-aminothiazol-4-yl)-2-carboxymethoxyiminoacetamido]-3-[(1-amino-1,4,5,6-tetrahydropyrimidin-3-ium)methyl]-ceph-3-em-4-carboxylate By following the procedure in Example 26 except that 0.36 g(3.6 mmol) of 1-amino-1,4,5,6-tetrahydropyrimidine was employed in place of 4-amino-1,2,4-triazole, there was obtained 0.37 g of the desired compound (23%).

Rf=0.29 (in 80% aqueous acetonitrile)
NMR (DMSO-d$_6$+20% DCl, δ) 1.5~1.85 (q, 2H), 3.3~3.92 (m, 6H, C-2) 4.69 (s, 2H), 5.2 (q, 2H, C-3) 5.29 (d, 1H, C-6), 5.8 (d, 1H, C-7) 7.05 (s, 1H, thiazole-H), 7.5 (s, 1H)

PREPARATION EXAMPLE 2

Synthesis of (6R,7R)-7-[(Z)-2-(2-aminothiazol-4-yl)-2-(2-carboxyprop-2-oxyimino)acetamido]-3-acetoxymethyl-ceph-3-em-4carboxylic acid A) A solution of 1.14 g(2 mmol) of (Z)-2-(2-tritylaminothiazol-4-yl)-2-(2-tert-butoxycarbonylprop-2-oxyimino) acetic acid and 0.88 g(2 mmol) of 7 β-amino-3-acetoxymethyl-ceph-3-em-4-carboxylate in 15 ml of N,N-dimethylformamide was stirred, cooled to 0°~5° C., and 0.30 g(2.2 mmol) of N-hydroxybenzotriazole hydrate and then 0.45 g(2.2 mmol) of N,N-dicyclohexylcarbodiimide were added thereto. The reaction mixture was stirred at room temperature for 6 hours and left to stand overnight. The reaction mixture was filtered and the filtered solid was washed with a small amount of diethyl ether. The filtrate and the washing were combined together, 100 ml of water was added followed by extraction with ethyl acetate. The organic layer was washed with water, 1N hydrochloric acid, sodium bicarbonate solution and then saturated brine, separated, dried over anhydrous sodium sulfate and concentrated under the reduced pressure. The concentrate was subjected to silica gel chromatography (eluent: 2% methanol/dichloromethane). The fractions containing the desired product were concentrated under the reduced pressure and crystallized from diisopropyl ether to give 1.49 g of diphenylmethyl (6R,7R)-7-[(Z)-2-(2-tritylaminothiazol-4-yl]-2-(2-tert-butoxycarbonylprop-2-oxyimino)acetamido]-3-acetoxymethyl-ceph-3-em-4-carboxylate as a desired product (75%).

B) In a mixed solvent of anisole(8 ml) and trifluoroacetic acid (15 ml) was dissolved 1.49 g of the product prepared in the above A) at 0° C. and the temperature was raised to room temperature. After stirring for 1.5 hours, the reaction solution was concentrated under the reduced pressure and 60 ml of diisopropyl ether was added to precipitate 700 mg of (6R,7R)-7-[(Z)-2-(2-aminothiazol-4-yl)-2-(2-carboxyprop-2-oxyimino)acetamido]-3-acetoxymethyl-ceph-3-em-4-carboxylic acid trifluoroacetate, which was filtered. Water(2.6 ml) was added to the solid and the pH was adjusted to 7.0 with saturated sodium bicarbonate solution. Purification by HP-20 chromatography (eluent: 70% aqueous acetonitrile) gave 0.55 g of (6R,7R)-7-[(Z)-2-(2-aminothiazol-4-yl)-2-(2-carboxypropoxyimino)acetamido]-3-acetoxymethyl-ceph-3-em-4-carboxylic acid (70%).

NMR (DMSO-$d_6$, δ) 1.32 (d, 6H), 2.22 (s, 3H), 3.52 (q, 2H, C-2) 4.87 (q, 2H, C-3), 5.2 (d, 1H, C-6), 5.75 (dd, 1H, C-7) 6.87 (s, 1H, thiazole-H)

EXAMPLE 32

Synthesis of (6R,7R)-7-[(Z)-2-(2-aminothiazol-4-yl)-2-(2-carboxyprop-2-oxyimino)acetamido]-3-[(1-amino-1,2,3,6-tetrahydropyridinium)methyl]-ceph-3-em-4-carboxylate In 15 ml of water was dissolved 3.75 g(25 mmol) of sodium iodide and the solution was heated to 70°~75° C. 0.59 g(6 mmol) of 1-amino-1,2,3,6-tetrahydropyridine was added and then, while adjusting the pH to 6.5~7.0, 2.64 g(5 mmol) of (6R,7R)-7-[(Z)-2-(2-aminothiazol-4-yl)-2-(2-carboxyprop-2-oxyimino)acetamido]-3-acetoxymethyl-ceph-3-em-4-carboxylic acid prepared in Preparation Example 2 was slowly added. The mixture was stirred at 70°~75° C. for 2 hours, cooled to room temperature and the pH was adjusted to 1~1.5 with 3N hydrochloric acid. The solution was stirred for 30 min and the precipitate was filtered off. The filtrate was concentrated under the reduced pressure, a small amount of water was added and subjected to HP-20 chromatography (80% aqueous acetonitrile). The fractions containing the desired product were concentrated under the reduced pressure and freeze-dried to give 0.51 g of the desired compound(18%).

NMR (DMSO-$d_6$+20% DCl, δ) 1.34 (d, 6H), 2.0~2.4 (m, 2H) 3.1~3.9 (m, 6H, C-2), 4.0~4.3 (m, 1H, C-3) 4.7~5.1 (m, 2H, C-3), 5.2~5.88 (m, 3H, C-7) 6.97 (s, 2H, thiazole-H)

EXAMPLE 33

Synthesis of (6R,7R)-7-[(Z)-2-(2-aminothiazol-4-yl)-2-(2-carboxyprop-2-oxyimino)acetamido]-3-(1-aminopiperidiniummethyl)-ceph-3-em-4-carboxylate By following the procedure in Example 32 except that 0.65 ml(6 mmol) of 1-aminopiperidine was employed in place of 1-amino-1,2,3,6-tetrahydropyridine, there was obtained 0.53 g of the desired compound (19%).

NMR (DMSO-$d_6$+20% DCl, δ) 1.30 (d, 6H), 1.5~2.3 (m, 6H) 3.2~4.3 (m, 7H), 4.78~5.1 (m, 1H, C-3) 5.2 (d, 1H, C-6), 5.7 (d, 1H, C-7) 7.02 (s, 1H, thiazole-H)

EXAMPLE 34

Synthesis of (6R,7R)-7-[(Z)-2-(2-aminothiazol-4-yl)-2-(2-carboxyprop-2-oxyimino)acetamido]-3-[(2-amino-1,2,3,4-tetrahydroisoquinolin-2-ium)methyl]-ceph-3-em-4-carboxylate By following the procedure in Example 32 except that 0.89 g(6 mmol) of 2-amino-1,2,3,4-tetrahydroisoquinoline was employed in place of 1-amino-1,2,3,6-tetrahydropyridine, there was obtained 0.52 g of the desired compound(17%).

NMR (DMSO-$d_6$+20% DCl, δ) 1.28 (d, 6H), 3.1~3.51 (m, 2H) 3.6~4.3 (m, 7H), 4.5~5.1 (m, 1H, C-3) 5.2 (dd, 1H, C-6), 5.75 (dd, 1H, C-7) 6.95 (s, 1H, thiazole-H), 7.1~7.7 (m, 4H, phenyl)

EXAMPLE 35

Synthesis of (6R,7R)-7-[(Z)-2-(2-aminothiazol-4-yl)-2-(2-carboxyprop-2-oxyimino)acetamido]-3-[(1-amino-1-methyl-4-piperazinium)methyl]-ceph-3-em-4-carboxylate By following the procedure in Example 32 except that 0.91 g(6 mmol) of 1-amino-1-methyl-4-piperazinium chloride hydrochloride was employed in place of 1-amino-1,2,3,6-tetrahydropyridine, there was obtained 0.94 g of the desired compound(32%).

NMR (DMSO-$d_6$+20% DCl, δ) 1.32 (d, 6H), 3.0~3.8 (m, 15H) 4.96 (d, 1H, C-6), 5.51 (d, 1H, C-7) 7.01 (s, 1H, thiazole-H)

EXAMPLE 36

Synthesis of (6R,7R)-7-[(Z)-2-(2-aminothiazol-4-yl)-2-(2-carboxyprop-2-oxyimino)acetamido]-3-[(4-amino-1,2,4-triazol-2-ium)methyl]-ceph-3-em-4-carboxylate In 8 ml of water was dissolved 2.75 g(15 mmol) of sodium iodide, the solution was heated to 70°~75° C.

and 0.3 g(3.6 mmol) of 4-amino-1,2,4-triazole was added. While adjusting the pH to 6.5~7, 1.5 g(3 mmol) of (6R,7R)-7-[(Z)-2-(2-aminothiazol-4-yl)-2-(2-carboxyprop-2-oxyimino) acetamido]-3-acetoxymethyl-ceph-3-em-4-carboxylic acid prepared in Preparation Example 2 was slowly added. The mixture was stirred at 70°~75° C. for 3 hours, cooled to room temperature and the pH was adjusted to 1~1.5 with 3N hydrochloric acid. The mixture was stirred for 30 min and the resulting precipitate was filtered off. The filtrate was concentrated under the reduced pressure, a small amount of water was added and subjected to HP-20 chromatography (80% aqueous acetionitrile). The fractions containing the desired product were concentrated under the reduced pressure and freeze-dried to give 0.35 g of the desired compound(20%).

MS(FAB, M+1)=552

NMR (DMSO-$d_6$+20% DCl, $\delta$) 1.30 (d, 6H), 3.3~3.6 (m, 2H, C-2) 5.07 (d, 1H, C-6), 5.0~5.37(q, 2H, C-3) 5.7 (d, 1H, C-7), 7.01 (s, 1H, thiazole-H) 8.7, 9.8 (s,s, 2H, triazole)

EXAMPLE 37

Synthesis of
(6R,7R)-7-[(Z)-2-(2-aminothiazol-4-yl)-2-(2-carboxyprop-2-oxyimino)acetamido]-3-[(1-aminoimidazol-3-ium)methyl]-ceph-3-em-4-carboxylate By following the procedure in Example 36 except that 0.3 g(3.6 mmol) of 1-aminoimidazole was employed in place of 4-amino-1,2,4-triazole, there was obtained 0.36 g of the desired compound(23%).

NMR (DMSO-$d_6$+20% DCl, $\delta$) 1.33 (d, 6H), 3.3~3.7 (m, 2H, C-2) 4.9~5.3 (m, 3H, C-6, C-3), 5.7 (d, 1H, C-7) 6.98 (s, 1H, thiazole-H), 7.7, 8.6 (s,s, 2H) 9.1 (t, 1H)

EXAMPLE 38

Synthesis of
(6R,7R)-7-[(Z)-2-(2-aminothiazol-4-yl)-2-(2-carboxyprop-2-oxyimino)acetamido]-3-[(1-aminopyrazol-2-ium)methyl]-ceph-3-em-4-carboxylate By following the procedure in Example 36 except that 0.3 g(3.6 mmol) of 1-aminopyrazole was employed in place of 4-amino-1,2,4-triazole, there was obtained 0.34 g of the desired compound(22%).

NMR (DMSO-$d_6$+20% DCl, $\delta$) 1.3 (d, 6H), 3.2~3.7 (m, 2H, C-2) 4.9~5.25 (m, 3H, C-3, C-6), 5.65 (d, 1H, C-7) 6.75 (s, 1H), 7.01 (s, 1H, thiazole-H) 7.8, 8.5 (s,s, 2H)

EXAMPLE 39

Synthesis of
(6R,7R)-7-[(Z)-2-(2-aminothiazol-4-yl)-2-(2-carboxyprop-2-oxyimino)acetamido]-3-[(1-aminoindazol-2-ium)methyl]-ceph-3-em-4-carboxylate By following the procedure in Example 36 except that 0.48 g(3.6 mmol) of 1-aminoindazole was employed in place of 4-amino-1,2,4-triazole, there was obtained 0.35 g of the desired compound(20%).

NMR (DMSO-$d_6$+20% DCl, $\delta$) 1.32 (d, 6H), 3.87~4.1 (m, 2H, C-2) 5.1~5.4 (m, 3H, C-3, C-6), 5.80 (d, 1H, C-7) 7.03 (s, 1H, thiazole-H), 7.1~8.2 (m, 4H, phenyl) 8.9 (s, 1H)

EXAMPLE 40

Synthesis of
(6R,7R)-7-[(Z)-2-(2-aminothiazol-4-yl)-2-(2-carboxyprop-2-oxyimino)acetamido]-3-[(1-aminobenzimidzol-3-ium)methyl]-ceph-3-em-4-carboxylate By following the procedure in Example 36 except that 0.48 g(3.6 mmol) of 1-aminobenzimidazole was employed in place of 4-amino-1,2,4-triazole, there was obtained 0.38 g of the desired compound(22%).

NMR (DMSO-$d_6$+20% DCl, $\delta$) 1.29 (d, 6H), 3.2~3.8 (m, 2H, C-2) 5.1~5.4 (m, 3H, C-3, C-6), 5.7 (d, 1H, C-7) 7.03 (s, 1H, thiazolo-H), 7.35~8.01 (m, 4H, phenyl) 9.7 (s, 1H, imidazole-H)

EXAMPLE 41

Synthesis of
(6R,7R)-7-[(Z)-2-(2-aminothiazol-4-yl)-2-(2-carboxyprop-2-oxyimino)acetamido]-3-[(1-amino-1,4,5,6-tetrahydropyrimidin-3-ium)methyl]-ceph-3-em-4-carboxylate By following the procedure in Example 36 except that 0.36 g(3.6 mmol) of 1-amino-1,4,5,6-tetrahydropyrimidine was employed in place of 4-amino-1,2,4-triazole, there was obtained 0.31 g of the desired compound(19%).

NMR (DMSO-$d_6$+20% DCl, $\delta$) 1.32 (d, 6H), 1.4~1.8 (q, 2H) 3.3~3.9 (m, 6H, C-2), 5.15~5.4 (m, 3H, C-3, C-6) 5.76 (d, 1H, C-7), 7.01 (s, 1H, thiazole-H) 8.5 (s, 1H)

PREPARATION EXAMPLE 3

Synthesis of
(6R,7R)-7-[(Z)-2-(2-aminothiazol-4-yl)-2-(2-carboxyprop-2-oxyimino)acetamido]-3-acetoxymethyl-ceph-3-em-4-carboxylic acid A) In 15 ml of N,N-dimethylformamide was dissolved 1.22 g(3 mmol) of (Z)-2-[(2-chloroacetamidothiazol-4-yl)-2-(2-tert-butoxycarbonylprop-2-oxyimino)acetic acid, 0.66 g(3.21 mmol) of N,N-dicyclohexylcarbodiimide was added thereto and the mixture was stirred at room temperature for 2 hours. 1.41 g(3.21 mmol) of diphenylmethyl 7$\beta$-amino-3-acetoxymethyl-ceph-3-em-4-carboxylate was added thereto at 0°~5° C. and the mixture was stirred at the same temperature for 4.5 hours.

After completion of the reaction, the insoluble was filtered off, 200 ml of dichloromethane was added to the filtrate and this was washed with diluted hydrochloric acid and then with water. The organic layer was dried over anhydrous magnesium sulfate and concentrated under the reduced pressure. The residue was purified by silica gel column chromatography using 6% methanol/dichloromethane as an eluent to give 1.86 g of diphenylmethyl (6R,7R)-7-[(Z)-2-(2-chloroacetamidothiazol-4-yl)-2-(2-tert-butoxycarbonylprop-2-oxyimino)acetamido]-3-acetoxymethyl-ceph-3-em-4-carboxylate in pale yellow powder form(70%).

B) In 15 ml of anisole was dissolved the product obtained in the above A), the solution was cooled to 0°~5° C. and 15 ml of trifluoroacetic acid was added thereto. The reaction mixture was stirred at the same temperature for 2 hours.

After completion of the reaction, the reaction solution was concentrated under the reduced pressure to remove trifluoroacetic acid. The residue was cooled to −20° ~ −10° C., 200 ml of diisopropyl ether was added and the mixture was stirred at the same temperature for 1 hour. The resulting precipitate was filtered, washed thoroughly with diisopropyl ether and dried to give 1.37 g of (6R,7R)-7-[(Z)-2-(2-chloroacetamidothiazol-4-yl)-2-(2-carboxyprop-2-oxyimino)acetamido]-3-acetoxymethyl-ceph-3-em-4-carboxylic acid trifluoroacetate (85%).

C) The product obtained in the above B) was suspended in 70 ml of water and the pH was adjusted to 6.5~7.0 with saturated sodium bicarbonate solution. 0.26 g(2 mmol) of sodium N-methyl-dithiocarbamate was added thereto and the mixture was stirred at room temperature for 5 hours.

After completion of the reaction, the reaction mixture was washed with ethyl acetate and the aqueous layer containing the desired product was concentrated under the reduced pressure. The concentrate was purified by HP-20 column chromatography. The fractions containing the desired product were concentrated under the reduced pressure and freeze-dried to give 0.73 g of (6R,7R)-[(Z)-2-(2-aminothiazol-4-yl)-2-(2-carboxyprop-2-oxyimino)acetamido]-3-acetoxymethyl-ceph-3-em-4-carboxylic acid(72%).

Rf=0.5 (in 80% aqueous acetonitrile)

The NMR spectra of the desired compound were the same as those of the compound obtained in Preparation Example 2.

EXAMPLE 42

Synthesis of (6R,7R)-7-[(Z)-2-(2-aminothiazol-4-yl)-2-(2-carboxyprop-2-oxyimino)acetamido]-3-[(4-aminomorpholin-4-ium)methyl]-ceph-3-em-4-carboxylate In a mixed solvent of acetonitrile(10 ml) and water(10 ml) was dissolved 6.69 g(50 mmol) of lithium iodide, 1.02 g(10 mmol) of 4-amino morpholine was added thereto and the mixture was heated to 65°~68° C. Water(4 ml) containing 2.64 g(5 mmol) of (6R,7R)-7-[(Z)-2-(2-aminothiazol-4-yl)-2-(2-carboxyprop-2-oxyimino)acetamido]-3-acetoxymethyl-ceph-3-em-4-carboxylic acid prepared in Preparation Example 3 and 0.1 g of sodium hydroxide was added thereto and the reaction mixture was stirred at 70°~72° C. for 1.5 hours while adjusting the pH to 6.5~7.0.

After completion of the reaction, the reaction solution was cooled to room temperature and the pH was adjusted to 1.5 with 3N hydrochloric acid. The insoluble was filtered off and the filtrate was concentrated under the reduced pressure followed by purification by column chromatography over aluminium oxide (eluent: 80% aqueous acetonitrile). The fractions were concentrated under the reduced pressure, dissolved in a small amount of water and purified by HP-20 column chromatography. The fractions containing the desired product were concentrated under the reduced pressure and freeze-dried to give 0.47 g of the desired compound (16%).

NMR (DMSO-$d_6$+20% DCl, δ) 1.3 (d, 6H), 3.35~4.55 (m, 11H) 4.95~5.36 (q, 1H, C-3), 5.34 (d, 1H, C-6) 5.8 (d, 1H, C-7), 7.02 (s, 1H, thiazole-H)

EXAMPLE 43

Synthesis of (6R, 7R)-7-[(Z)-2-(2-aminothiazol-4-yl)-2-(2-carboxyprop-2-oxyimino)acetamido]-3-(1-aminopyrrolidiniummethyl)-ceph-3-em-4-carboxylate By following the procedure in Example 42 except that 1.23 g(10 mmol) of 1-aminopyrrolidine was employed in place of 4-aminomorpholine, there was obtained 0.51 g of the desired compound(18%).

NMR (DMSO-$d_6$+20% DCl, δ) 1.34 (d, 6H), 1.75~2.25 (m, 4H) 2.92~3.75 (m, 6H), 3.8~4.2 (m, 1H, C-3) 4.4~5.0 (m, 1H, C-3), 5.2 (d, 1H, C-6) 5.7 (d, 1H, C-7), 7.02 (s, 1H, thiazole-H)

EXAMPLE 44

Synthesis of (6R,7R)-7-[(Z)-2-(2-aminothiazol-4-yl)-2-(2-carboxyprop-2-oxyimino)acetamido]-3-[(1-amino-3-pyrrolin-1-ium)methyl]-ceph-3-em-4-carboxylate By following the procedure in Example 42 except that 0.84 g(10 mmol) of 1-amino-3-pyrroline was employed in place of 4-aminomorpholine, there was obtained 0.39 g of the desired compound(14%).

NMR (DMSO-$d_6$+20% DCl, δ) 1.30 (d, 6H), 3.6~4.1 (m, 3H, C-2, C-3) 4.65 (s, 4H), 4.57~5.1 (m, 1H, C-3) 5.2 (d, 1H, C-6), 5.65 (d, 1H, C-7) 7.03 (s, 1H, thiazole-H)

EXAMPLE 45

Synthesis of (6R,7R)-7-[(Z)-2-(2-aminothiazol-4-yl)-2-(2-carboxyprop-2-oxyimino)acetamido]-3-(1-aminoindoliniummethyl)-ceph-3-em-4-carboxylate By following the procedure in Example 42 except that 1.34 g(10 mmol) of 1-aminoindoline was employed in place of 4-aminomorpholine, there was obtained 0.48 g of the desired compound(16%).

NMR (DMSO-$d_6$+20% DCl, δ) 1.32 (d, 6H), 2.8~3.2 (m, 2H) 3.4~4.5 (m, 5H), 4.6~5.2 (m, 2H, C-3, C-6) 5.65 (d, 1H, C-7), 7.01 (s, 1H, thiazole-H) 7.05~7.8 (m, 4H, phenyl)

EXAMPLE 46

Synthesis of (6R,7R)-7[(Z)-2-(2-aminothiazol-4-yl)-2-(2-carboxyprop-2-oxyimino)acetamido]-3-(1-aminopyrroliummethyl)-ceph-3-em-4-carboxylate By following the procedure in Example 42 except that 0.82 g(10 mmol) of 1-aminopyrrole was employed in place of 4-aminomorpholine, there was obtained 0.45 g of the desired compound(16%).

NMR (DMSO-$d_6$+20% DCl, δ) 1.28 (d, 6H), 3.64 (m, 3H, C-2, C-3) 4.6~5.2 (m, 2H, C-3, C-6), 5.6 (d, 1H, C-7) 6.2 (t, 2H), 6.6 (t, 2H) 7.03 (s, 1H, thiazole-H)

EXAMPLE 47

Synthesis of (6R,7R)-7-[(Z)-2-(2-aminothiazol-4-yl)-2-(2-carboxyprop-2-oxyimino)acetamido]-3-(1-aminoindolIummethyl)-ceph-3-em-4-carboxylate By following the procedure in Example 42 except that 1.32 g(10 mmol) of 1-aminoindole was employed in place of 4-aminomorpholine, there was obtained 0.49 g of the desired compound(16%).

NMR (DMSO-d$_6$+20% DCl, δ) 1.29 (d, 6H), 3.5~4.0 (m, 3H, C-2, C-3) 4.6~5.2 (m, 2H, C-3, C-6), 5.65 (d, 1H, C-7) 6.5 (d, 1H), 7.02 (s, 1H, thiazole-H) 7.05~7.9 (m, 5H, phenyl)

EXAMPLE 48

Synthesis of (6R,7R)-7-[(Z)-2-(2-aminothiazol-4-yl)-2-(2-carboxyprop-2-oxyimino)acetamido]-3-[(1-amino-4-hydroxypiperidinium)methyl]-ceph-3-em-4-carboxylate By following the procedure in Example 42 except that 1.16 g(10 mmol) of 1-amino-4-hydroxypiperidine was employed in place of 4-aminomorpholine, there was obtained 0.51 g of the desired compound(17%).

Rf=0.14 (in 80% aqueous acetonitrile)

NMR (20% DCl, δ) 1.18~2.0 (m, 4H), 1.30 (d, 6H) 3.2~4.3 (m, 7H), 4.86~5.2 (m, 2H, C-3) 5.35 (d, 1H, C-6), 5.93 (d, 1H, C-7) 7.21 (s, 1H, thiazole-H)

EXAMPLE 49

Synthesis of (6R,7R)-7-[(Z)-2-(2-aminothiazol-4-yl)-2-(2-carboxyprop-2-oxyimino)acetamido]-3-[(1-amino-1,2,3-triazol-3-ium)methyl]-ceph-3-em-4-carboxylate In a mixed solvent of acetonitrile(10 ml) and water(15 ml) was dissolved 5.35 g(40 mmol) of lithium iodide, 0.673 g(8 mmol) of 1-amino-1,2,3-triazole was added thereto and the mixture was heated to 65°~68° C. 2.11 g(4 mmol) of (6R,7R)-7-[(Z)-2-(2-aminothiazol-4-yl)-2-(2-carboxyprop-2-oxyimino)acetamido]-3-acetoxymethyl-ceph-3-em-4-carboxylic acid prepared in Preparation Example 3 was added and the mixture was stirred at 70°~72° C. for 2 hours while adjusting the pH to 6.5~7.0.

After completion of the reaction, the reaction solution was cooled to room temperature and the pH was adjusted to 1~1.5 with 3N hydrochloric acid. The insoluble was filtered off and the filtrate was concentrated under the reduced pressure followed by column chromatography over aluminium oxide using 80% aqueous acetonitrile solution as an eluent. The fractions were concentrated under the reduced pressure, dissolved in a small amount of water and purified by HP-20 column chromatography. The fractions containing the desired product were concentrated under the reduced pressure and freeze-dried to give 0.68 g of the desired compound(31%).

NMR (DMSO-d$_6$+20% DCl, δ) 1.3 (d, 6H), 3.4~3.7 (m, 2H, C-2) 5.05~5.18 (m, 3H, C-3, C-6), 5.67 (d, 1H, C-7) 7.02 (s, 1H, thiazole-H), 7.8, 8.7 (s,s, 2H, triazole-H)

EXAMPLE 50

Synthesis of (6R,7R)-7-[(Z)-2-(2-aminothiazol-4-yl)-2-(2-carboxyprop-2-oxyimino)acetamido]-3-[(1-aminobenzotriazol-3-ium)methyl]-ceph-3-em-4-carboxylate By following the procedure in Example 49 except that 1.07 g(8 mmol) of 1-aminobenzotriazole was employed in place of 1-amino-1,2,3-triazole, there was obtained 0.53 g of the desired compound(22%).

MS(FAB, M+1)=602

NMR (DMSO-d$_6$+20% DCl, δ) 1.31 (d, 6H), 3.86~4.1 (m, 2H, C-2) 5.05~5.55 (m, 3H, C-3, C-6), 5.87 (d, 1H, C-7) 7.02 (s, 1H), 7.7~8.15 (m, 4H, phenyl)

EXAMPLE 51

Synthesis of (6R,7R)-7-[(Z)-2-(2-aminothiazol-4-yl)-2-(2-carboxyprop-2-oxyimino)acetamido]-3-[(1-amino-1,2,4-triazol-4-ium)methyl]-ceph-3-em-4-carboxylate By following the procedure in Example 49 except that 0.67 g(8 mmol) of 1-amino-1,2,4-triazole was employed in place of 1-amino-1,2,3-triazole, there was obtained 0.5 g of the desired compound(23%).

NMR (DMSO-d$_6$+20% DCl, δ) 1.28 (d, 6H), 3.29~3.74 (m, 2H, C-2) 5.05~5.25 (m, 3H, C-3, C-6), 5.7 (d, 1H, C-7) 6.94 (s, 1H, thiazole-H), 8.74, 9.68 (s,s, 2H, triazole)

EXAMPLE 52

Synthesis of (6R,7R)-7-[(Z)-2-(2-aminothiazol-4-yl)-2-(2-carboxyprop-2-oxyimino)acetamido]-3-[(1-aminotetrazol-4-ium)methyl]-ceph-3-em-4-carboxylate By following the procedure in Example 49 except that 0.69 g (8 mmol) of 1-aminotetrazole was employed in place of 1-amino-1,2,3-triazole, there was obtained 0.48 g of the desired compound (22%).

NMR (DMSO-d$_6$+20% DCl, δ) 1.29 (d, 3H), 3.3~3.76 (m, 2H, C-2) 5.05~5.2 (m, 3H, C-3, C-6), 5.7 (d, 1H, C-7) 6.99 (s, 1H, thiazole-H), 9.52 (s, 1H, tetrazole-H)

PREPARATION EXAMPLE 4

Synthesis of (6R,7R)-7-[(Z)-2-(2-aminothiazol-4-yl)-2-carboxymethoxyiminoacetamido]-3-acetoxymethyl-ceph-3-em-4-carboxylic acid A) In 15 ml of N,N-dimethylformamide was dissolved 1.13 g(3 mmol) of (Z)-2-[(2-chloroacetamidothiazol-4-yl)-2-tert-butoxycarbonylmethoxyimino]acetic acid, and 0.43 g(3.18 mmol) of N-hydroxybenzotriazole and 0.66 g(3.21 mmol) of N,N-dicyclohexylcarbodiimide were added thereto. The reaction mixture was stirred at room temperature for 2 hours.

1.41 g(3.21 mmol) of diphenylmethyl 7 β-amino-3-acetoxymethyl-ceph-3-em-4-carboxylate was added at 0°~5° C. and the mixture was stirred at the same temperature for 5 hours. After completion of the reaction, the procedure in Preparation Example 3-A) was repeated to give 1.67 g of diphenylmethyl(6R,7R)-7-[(Z)-2-(2-chloroacetamidothiazol-4-yl)-2-tert-butoxycarbonylmethoxyiminoacetamido]-3-acetoxymethyl-ceph-3-em-4-carboxylate(65%).

B) The product obtained in the above A) was dissolved in 120 ml of anisole and the mixture was cooled to 0°~5° C. 12 ml of trifluoroacetic acid was added and the reaction mixture was stirred at the same temperature for 2 hours. After completion of the reaction, the procedure in Preparation Example 3-B) was repeated to give 1.2 g of (6R,7R)-7-[(Z)-2-(2-chloroacetamidothiazol-4-yl)-2-carboxymethoxyiminoacetamido]-3-acetoxymethyl-ceph-3-em-4-carboxylic acid trifluoroacetate(83%).

C) The product obtained in the above B) was suspended in 65 ml of water and the pH was adjusted to 6.5~7.0 with saturated sodium bicarbonate solution. 0.34 g(2.6 mmol) of sodium N-methyl-dithiocarba-mate was added and the reaction mixture was stirred at room temperature for 4~5 hours. After completion of the reaction, the procedure in Preparation Example 3-C) was repeated to give 582 mg of (6R,7R)-7-[(Z)-2-(2-aminothiazol-4-yl)-2-carboxymethoxyiminoacetamido]-3-acetoxymethyl-ceph-3-em-4-carboxylic acid (67%).

Rf=0.65 (in 80% aqueous acetonitrile)

NMR (DMSO-$d_6$, $\delta$) 2.11 (s, 3H), 3.25~3.82 (q, 2H, C-2) 4.6 (s, 2H), 4.79~4.89 (d, 2H) 5.19~5.25 (d, 1H, C-6), 5.79~5.85 (dd, 1H, C-7) 6.71 (s, 1H, thiazole-H), 7.27 (br, 2H, NH$_2$) 9.5 (d, 1H, -NH)

EXAMPLE 53

Synthesis of (6R,7R)-7-[(Z)-2-(2-aminothiazol-4-yl)-2-carboxymethoxyiminoacetamido]-3-[(4-aminomorpholin-4-1um)-methyl]-ceph-3-em-4-carboxylate In a mixed solvent of acetonitrile(9 ml) and water(10 ml) was dissolved 6.69 g(50 mmol) of lithium iodide, the solution was heated to 65°~68° C. and 1.02 g(10 mmol) of 4-aminomorpholine was added thereto. Water (3 ml) containing 2.5 g(5 mmol) of (6R,7)-7-[(Z)-2-(2-aminothiazol-4-yl)-2-carboxymethoxyiminoacetamido]-3-acetoxymethyl-ceph-3-em-4-carboxylic acid and 0.1 g of sodium hydroxide was added and the reaction mixture was stirred at 70°~73° C. for 2 hours while the pH was adjusted to 6.5~7.0.

After completion of the reaction, the reaction solution was cooled to room temperature and the pH was adjusted to 1.5 with 3N hydrochloric acid. The insoluble was filtered off and the filtrate was concentrated under the reduced pressure followed by aluminium oxide column chromatography using 80% aqueous acetonitrile as an eluent. The fractions were concentrated under the reduced pressure, dissolved in a small amount of water and purified by HP-20 column chromatography. The fractions containing the desired product were concentrated under the reduced pressure and freeze-dried to give 0.79 g of the desired compound(29%).

Rf=0.34 (in 80% aqueous acetonitrile)

NMR (20% DCl, $\delta$) 3.4~4.6 (m, 11H, morpholine, C-2, C-3), 4.7 (s, 2H) 5.0~5.35 (q, 1H, C-3), 5.33 (d, 1H, C-6) 5.8 (d, 1H, C-7), 7.18 (s, 1H, thiazole-H)

EXAMPLE 54

Synthesis of (6R,7R)-7-[(Z)-2-(2-aminothiazol-4-yl)-2-carboxymethoxyiminoacetamido]-3-(1-aminopyrrolidiniummethyl)-ceph-3-em-4-carboxylate By following the procedure in Example 53 except that 1.23g(10 mmol) of 1-aminopyrrolidine was employed in place of 4-aminomorpholine, there was obtained 0.49 g of the desired compound(19%).

Rf=0.3 (in 80% aqueous acetonitrile)

NMR (20% DCl, $\delta$) 1.75~2.3 (m, 4H, pyrrolidine), 2.91~3.8 (m, 6H, C-2, pyrrolidine) 3.9~4.4 (m, 1H, C-3), 4.65 (s, 2H) 4.5~4.95 (m, 1H, C-3), 5.15 (dd, 1H, C-6) 5.7 (dd, 1H, C-7), 7.12 (s, 1H, thiazole-H)

EXAMPLE 55

Synthesis of (6R,7R)-7-[(Z)-2-(2-aminothiazol-4-yl)-2-carboxymethoxyiminoacetamido]-3-[(1-amino-3-pyrrolin-1-ium)-methyl]-ceph-3-em-4-carboxylate By following the procedure in Example 53 except that 0.84 g(10 mmol) of 1-amino-3-pyrroline was employed in place of 4-aminomorpholine, there was obtained 0.47 g of the desired compound(18%).

Rf=0.3 (in 80% aqueous acetonitrile)

NMR (DMSO-$d_6$+20% DCl, $\delta$) 3.5~4.1 (m, 3H, C-2, C-3), 4.6 (s, 4H, pyrroline) 4.56~5.1 (m, 1H, C-3), 4.7 (s, 2H) 5.16 (d, 1H, C-6), 5.7 (d, 1H, C-7) 5.92 (s, 2H, pyrroline), 7.04 (s, 1H, thiazole-H)

EXAMPLE 56

Synthesis of (6R,7R)-7-[(Z)-2-(2-aminothiazol-4-yl)-2-carboxymethoxyiminoacetamido]-3-(1-aminoindoliniummethyl)-ceph-3-em-4-carboxylate By following the procedure in Example 53 except that 1.34 g(10 mmol) of 1-aminoindoline was employed in place of 4-aminomorpholine, there was obtained 0.5 g of the desired compound(17%).

Rf=0.37 (in 80% aqueous acetonitrile)

NMR (DMSO-$d_6$+20% DCl, $\delta$) 2.8~3.2 (m, 2H, indole) 3.4~4.4 (m, 5H, indole, C-2, C-3), 4.65 (s, 2H) 4.7~5.1 (m, 1H, C-3), 5.12 (d, 1H, C-6) 5.7 (d, 1H, C-7), 7.02 (s, 1H, thiazole-H) 7.04~7.8 (m, 4H, phenyl)

EXAMPLE 57

Synthesis of (6R,7R)-7-[(Z)-2-(2-aminothiazol-4-yl)-2-carboxymethoxyiminoacetamido]-3-(1-aminopyrroliummethyl)-ceph-3-em-4-carboxylate By following the procedure in Example 53 except that 0.82 g(10 mmol) of 1-aminopyrrole was employed in place of 4-aminomorpholine, there was obtained 0.43 g of the desired compound(16%).

Rf=0.28 (in 80% aqueous acetonitrile)

NMR (DMSO-$d_6$+20% DCl, $\delta$) 3.6~4.0 (m, 3H, C-2, C-3), 4.65 (s, 2H) 4.6~5.0 (m, 1H, C-3), 5.2 (d, 1H, C-6) 5.65 (d, 1H, C-7), 6.12 (t, 2H, pyrrole) 6.5 (t, 2H, pyrrole), 7.03 (s, 1H, thiazole-H)

EXAMPLE 58

Synthesis of (6R,7R)-7-[(Z)-2-(2-aminothiazol-4-yl)-2-carboxymethoxyiminoacetamido]-3-(1-aminoindoliummethyl)-ceph-3-em-4-carboxylate By following the procedure in Example 53 except that 1.32 g(10 mmol) of 1-aminoindole was employed in place of 4-aminomorpholine, there was obtained 0.41 g of the desired compound(14%).

Rf=0.35 (in 80% aqueous acetonitrile)

NMR (DMSO-$d_6$+20% DCl, $\delta$) 3.47~4.0 (m, 3H, C-2, C-3), 4.62~5.0 (m, 1H, C-3) 4.7 (s, 2H), 5.2 (d, 1H, C-6) 5.55 (d, 1H, C-7), 6.47 (d, 1H, indole) 7.01 (s, 1H, thiazole-H), 7.03~8.0 (m, 5H, phenyl)

EXAMPLE 59

Synthesis of (6R,7R)-7-[(Z)-2-(2-aminothiazol-4-yl)-2-carboxymethoxyiminoacetamido]-3-[(1-amino-4-hydroxypiperidinium)methyl]-ceph-3-em-4-carboxylate By following the procedure in Example 53 except that 1.16 g(10 mmol) of 1-amino-4-hydroxypiperidine was employed in place of 4-aminomorpholine, there was obtained 0.56 g of the desired compound(20%).

Rf=0.14 (in 80% aqueous acetonitrile)

NMR (20% DCl, $\delta$) 1.2~2.0 (m, 4H), 3.22~4.4 (m, 7H) 4.70 (s, 2H), 4.85~5.21 (m, 2H, C-3) 5.35 (d, 1H, C-6), 5.95 (d, 1H, C-7) 7.22 (s, 1H, thiazole-H)

EXAMPLE 60

Synthesis of
(6R,7R)-7-[(Z)-2-(2-aminothiazol-4-yl)-2-carboxymethoxyiminoacetamido]-3-[(1-amino-1,2,3-triazol-3-ium)-methyl]-ceph-3-em-4-carboxylate In a mixed solvent of acetonitrile (9 ml) and water(15 ml) was dissolved 5.35 g(40 mmol) of lithium iodide, 0.673 g(8 mmol) of 1-amino-1,2,3-triazole was added thereto and the mixture was heated to 68° C. 2 g(4 mmol) of (6R,7R)-7-[(Z)-2-(2-aminothiazol-4-yl)-2-carboxymethoxyiminoacetamido]-3-acetoxymethyl-ceph-3-em-4-carboxylic acid prepared in Preparation Example 4 was added and the mixture was stirred at 70°~72° C. for 1.5 hours while adjusting the pH to 6.5~7.0.

After completion of the reaction, the reaction solution was cooled to room temperature and the pH was adjusted to 1.5 with 3N hydrochloric acid. The insoluble was filtered off and the filtrate was concentrated under the reduced pressure followed by aluminium oxide column chromatography using 80% aqueous acetonitrile as an eluent. The fractions were concentrated under the reduced pressure, dissolved in a small amount of water and purified by HP-20 column chromatography. The fractions containing the desired product were concentrated under the reduced pressure and freeze-dried to give 0.48 g of the desired compound(23%).

Rf=0.25 (in 80% aqueous acetonitrile)

NMR (DMSO-$d_6$+20% DCl, $\delta$) 3.4~3.72 (m, 2H, C-2), 4.75 (s, 2H), 5.13 (q, 2H, C-3) 5.16 (d, 1H, C-6), 5.7 (d, 1H, C-7) 7.02 (s, 1H, thiazole-H), 7.8, 8.8 (s,s, 2H, triazole)

EXAMPLE 61

Synthesis of
(6R,7R)-7-[(Z)-2-(2-aminothiazol-4-yl)-2-carboxymethoxyiminoacetamido]-3-[1-aminobenzotriazol-3-ium)-methyl]-ceph-3-em-4-carboxylate By following the procedure in Example 60 except that 1.07 g(8 mmol) of 1-aminobenzotriazole was employed in place of 1-amino-1,2,3-triazole, there was obtained 0.51 g of the desired compound(22%).

Rf=0.3 (in 80% aqueous acetonitrile)

MS(FAB, M+1)=574

NMR (DMSO-$d_6$+20% DCl, $\delta$) 3.82~4.1 (m, 2H, C-2), 4.72 (s, 2H) 5.1~5.45 (q, 2H, C-3), 5.35 (d, 1H, C-6) 5.85 (d, 1H, C-7), 7.02 (s, 1H, thiazole-H) 7.5~8.2 (m, 4H, phenyl)

EXAMPLE 62

Synthesis of
(6R,7R)-7-[(Z)-2-(2-aminothiazol-4-yl)-2-carboxymethoxyiminoacetamido]-3-[(1-amino-1,2,4-triazol-4-ium)-methyl]-ceph-3-em-4-carboxylate By following the procedure in Example 60 except that 0.67 g(8 mmol) of 1-amino-1,2,4-triazole was employed in place of 1-amino-1,2,3-triazole, there was obtained 0.53 g of the desired compound (25%).

Rf=0.3 (in 80% aqueous acetonitrile)

NMR (DMSO-$d_6$+20% DCl, $\delta$) 3.4~3.8 (m, 2H, C-2), 4.65 (s, 2H) 5.12 (q, 2H, C-3), 5.2 (d, 1H, C-6) 5.6 (d, 1H, C-7), 6.99 (s, 1H, thiazole-H) 8.75, 9.68 (s,s, 2H, triazole)

EXAMPLE 63

Synthesis of
(6R,7R)-7-[(Z)-2-(2-aminothiazol-4-yl)-2-carboxymethoxyiminoacetamido]-3-[(1-aminotetrazol-4-ium)methyl]-ceph-3-em-4-carboxylate By following the procedure in Example 60 except that 0.69 g(8 mmol) of 1-aminotetrazole was employed in place of 1-amino-1,2,3-triazole, there was obtained 0.43 g of the desired compound(19%).

Rf=0.24 (in 80% aqueous acetonitrile)

NMR (DMSO-$d_6$+20% DCl, $\delta$) 3.23~3.8 (m, 2H, C-2), 4.68 (s, 2H) 5.1 (q, 2H, C-3), 5.25 (d, 1H, C-6) 5.7 (d, 1H, C-7), 7.05 (s, 1H, thiazole-H) 9.6 (s, 1H, tetrazole-H)

PREPARATION EXAMPLE 5

Synthesis of
(6R,7R)-7-[(Z)-2-(2-tritylaminothiazol-4-yl)-2-methoxyiminoacetamido]-3-chloromethyl-ceph-3-em-4-carboxylate To 10 ml of dichloromethane were added 0.45 g(1 mmol) of diphenylmethyl 7$\beta$-amino-3-chloromethyl-ceph-3-em-4-carboxylate hydrochloride and 0.53 g (1.2 mmol) of (Z)-2-(2-tritylaminothiazol-4-yl)-2-methoxyiminoacetic acid. 0.4 ml(5 mmol) of pyridine and 0.11 ml(1.2 mmol) of phosphorus oxychloride were slowly added under ice-cooling and the mixture was stirred for 15 min. 50 ml of chloroform was added, and the mixture was washed with water and dried over anhydrous sodium sulfate.

The solution was concentrated under the reduced pressure and subjected to silica gel chromatography (2% methanol/dichloromethane). The fractions containing the desired product were concentrated under the reduced pressure and crystallized from diisopropyl ether to give 0.6 g of the desired compound(72%).

NMR (CDCl$_3$, $\delta$) 3.55 (bs, 2H), 4.05 (s, 3H), 4.30 (bs, 2H) 5.05 (d, 1H), 5.90 (dd, 1H), 6.75 (s, 1H) 6.95 (s, 1H), 7.1~7.8 (m, 26H)

PREPARATION EXAMPLE 6

Synthesis of diphenylmethyl
(6R,7R)-7-[(Z)-2-(2-tritylaminothiazol-4-yl)-2-methoxyiminoacetamido]-3-chloromethyl-ceph-3-em-4-carboxylate To 25 ml of N,N-dimethylformamide were added 1.3 g (3 mmol) of (Z)-2-(2-tritylaminothiazol-4-yl)-2-methoxyiminoacetic acid and 1.35 (3 mmol) of diphenylmethyl 7 $\beta$-amino-3-chloromethyl-ceph-3-em-4-carboxylate hydrochloride. The mixture was cooled to 0° C., and 0.53 g (3.9 mmol) of N-hydroxybenzotriazole hydrate and then 0.80 g (3.9 mmol) of N,N-dicyclohexylcarbodiimide were added thereto.

The reaction mixture was stirred for 5 hours and left to stand overnight. The reaction mixture was filtered and the filtered solid was washed with a small amount of diethyl ether. The filtrate and the washing were combined together and 125 ml of water was added thereto. The reaction mixture was extracted with ethyl acetate and washed with sodium bicarbonate solution and then saturated brine. The organic layer was dried over anhydrous sodium sulfate, concentrated under the reduced pressure and subjected to silica gel chromatography (2% methanol/dichloromethane). The fractions containing the desired product were concentrated under the reduced pressure and crystallized from diisopropyl ether to give 1.92 g of the desired compound(76%).

NMR (CDCl$_3$, δ) 3.55 (bs, 2H), 4.05 (s, 3H), 4.30 (bs, 2H) 5.05 (d, 1H), 5.90 (dd, 1H), 6.75 (s, 1H) 6.95 (s, 1H), 7.1~7.8 (m, 26H)

EXAMPLE 64

Synthesis of (6R,7R)-7-[(Z)-2-(2-aminothiazol-4-yl)-2-methoxyiminoacetamido]-3-(1-aminopiperidiniummethyl)-ceph-3-em-4-carboxylate A) In 5 ml of N,N-dimethylformamide were dissolved 2.52 g(3.0 mmol) of diphenylmethyl (6R,7R)-7-[(Z)-2-(2-tritylaminothiazol-4-yl)-2-methoxyiminoacetamido]-3-chloromethyl-ceph-3-em-4-carboxylate prepared in Preparation Example 5 or 6 and 0.67 g(0.45 mmol) of sodium iodide and 0.39 ml (3.6 mmol) of 1-aminopiperidine was added thereto. The mixture was stirred at room temperature for 3 hours. To the reaction solution was added 15 ml of water and the mixture was extracted with dichloromethane. The organic layer was washed with water, dried over anhydrous magnesium sulfate, concentrated under the reduced pressure and subjected to silica gel chromatography (4% methanol/dichloromethane). The fractions containing the desired product were concentrated under the reduced pressure to give 1.86 g of diphenylmethyl (6R,7R)-7-[(Z)-2-(2-tritylaminothiazol-4-yl)-2-methoxyiminoacetamido]-3-(1-aminopiperidinium methyl)-ceph-3-em-4-carboxylate iodide(60%).

B) To 1.7 ml of anisole was added 0.6 g(0.58 mmol) of the product obtained in the above A), 5.6 ml of trifluoroacetic acid was slowly added under ice-cooling and the mixture was stirred for 1 hour. Diisopropyl ether was added, and the resulting precipitate was filtered and dried. A small amount of water was added to the solid, and the pH was adjusted to 5~8 with saturated sodium bicarbonate solution. HP-20 colum chromatography was carried out by using 80% aqueous acetonitrile solution as an eluent. The fractions containing the desired product were concentrated under the reduced pressure and freeze-dried to give 0.24 g of the desired compound (82%).

The NMR spectra of the desired compound were the same as those of the compound prepared in Example 3.

EXAMPLE 65

Synthesis of (6R,7R)-7-[(Z)-2-(2-aminothiazol-4-yl)-2-methoxyiminoacetamido]-3-[(4-aminomorpholin-4-ium)methyl]-ceph-3-em-4-carboxylate By following the procedure in Example 64 except that 0.35 g(3.6 mmol) of 4-aminomorpholine was employed in place of 1-aminopiperidine, there was obtained 0.63 g of the desired compound (43%).

The NMR spectra of the desired compound were the same as those of the compound prepared in Example 2.

EXAMPLE 66

Synthesis of (6R,7R)-7-[(Z)-2-(2-aminothiazol-4-yl)-2-methoxyiminoacetamido]-3-(1-aminopyrrolidiniummethyl)-ceph-3-em-4-carboxylate By following the procedure in Example 64 except that 0.44 g(3.6 mmol) of 1-aminopyrrolidine was employed in place of 1-aminopiperidine, there was obtained 0.65 g of the desired compound (45%).

The NMR spectra of the desired compound were the same as those of the compound prepared in Example 1.

EXAMPLE 67

Synthesis of (6R,7R)-7-[(Z)-2-(2-aminothiazol-4-yl)-2-methoxyiminoacetamido]-3-[(1-amino-1,2,3,6-tetrahydropyridinium)methyl]-ceph-3-em-4-carboxylate By following the procedure in Example 64 except that 0.53 g(3.6 mmol) of 1-amino-1,2,3,6-tetrahydropyridine was employed in place of 1-aminopiperidine, there was obtained 0.54 g of the desired compound (36%).

The NMR spectra of the desired compound were the same as those of the compound prepared in Example 8.

EXAMPLE 68

Synthesis of (6R,7R)-7-[(Z)-2-(2-aminothiazol-4-yl)-2-methoxyiminoacetamido]-3-[(1-amino-4-hydroxypiperidinium)methyl]-ceph-3-em-4-carboxylate By following the procedure in Example 64 except that 0.42 g(3.6 mmol) of 1-amino-4-hydroxypiperidine was employed in place of 1-aminopiperidine, there was obtained 0.65 g of the desired compound (42%).

The NMR spectra of the desired compound were the same as those of the compound prepared in Example 4.

EXAMPLE 69

Synthesis of (6R,7R)-7-[(Z)-2-(2-aminothiazol-4-yl)-2-methoxyiminoacetamido]-3-[(2-amino-1,2,3,4-tetrahydroisoquinolin-2-ium)methyl]-ceph-3-em-4-carboxylate By following the procedure in Example 64 except that 0.53 g(3.6 mmol) of 2-amino-1,2,3,4-tetrahydroisoquinoline was employed in place of 1-aminopiperidine, there was obtained 0.78 g of the desired compound (48%).

The NMR spectra of the desired compound were the same as those of the compound prepared in Example 5.

EXAMPLE 70

Synthesis of (6R,7R)-7-[(Z)-2-(2-aminothiazol-4-yl)-2-methoxyiminoacetamido]-3-[(1-amino-1-methyl-4-piperazinium)methyl]-ceph-3-em-4-carboxylate By following the procedure in Example 64 except that 0.55 g(3.6 mmol) of 1-amino-1-methyl-4-piperazinium was employed in place of 1-aminopiperidine, there was obtained 1.14 g of the desired compound (75%).

The NMR spectra of the desired compound were the same as those of the compound prepared in Example 11.

EXAMPLE 71

Synthesis of (6R,7R)-7-[(Z)-2-(2-aminothiazol-4-yl)-2-methoxyiminoacetamido]-3-[(4-amino-1,2,4-triazol-2-ium)methyl]-ceph-3-em-4carboxylate A) In 5 ml of N,N-dimethylformamide were dissolved 2.52 g(3.0 mmol) of diphenylmethyl (6R,7R)-7-[(Z)-2-(2-tritylaminothiazol-4-yl)-2-methoxyiminoacetamido]-3-chloromethyl-ceph-3-em-4-carboxylate prepared in Preparation Example 5 or 6 and 1.35 g(9.0 mmol) of sodium iodide and 0.34 g(4.0 mmol) of 4-amino-1,2,4-triazole was added thereto. The reaction mixture was stirred at 45°~50° C. for 3 hours and cooled to room temperature. 15 ml of water was added, the reaction mixture was extracted with dichloromethane and the organic layer was washed with water. The dichloromethane layer was dried over anhydrous magnesium sulfate, concentrated under the reduced pressure and subjected to silica gel chromatography (5% methanol/dichloromethane). The fractions containing the desired product were concentrated under the reduced pressure to give 1.71 g of diphenylmethyl (6R,7R)-7-[(Z)-2-(2-tritylaminothiazol-4-yl)-2-methoxyiminoacetamido]-3-[(4-amino-1,2,4-triazol-2-ium)methyl]-ceph-3-em-4-carboxylate iodide(56%).

B) To 1.6 ml of anisole was added 0.56 g(0.55 mmol) of the compound prepared in the above A), 5.5 ml of trifluoroacetic acid was slowly added under ice-cooling and the mixture was stirred for 1 hour. Diisopropyl ether was added, and the resulting precipitate was filtered and dried. A small amount of water was added, the pH was adjusted to 4.5~5 with saturated sodium bicarbonate solution and the solution was subjected to HP-20 column chromatography using 80% aqueous acetonitrile as an eluent. The fractions containing the desired product were concentrated under the reduced pressure and freeze-dried to give 0.21 g of the desired compound (78%).

The NMR spectra of the desired compound were the same as those of the compound prepared in Example 12.

EXAMPLE 72

Synthesis of
(6R,7R)-7-[(Z)-2-(2-aminothiazol-4-yl)-2-methoxyiminoacetamido]-3-[(1-amino-1,2,4-triazol-4-ium)methyl]-ceph-3-em-4-carboxylate By following the procedure in Example 71 except that 0.34 g(4 mmol) of 1-amino-1,2,4-triazole was employed in place of 4-amino-1,2,4-triazole, there was obtained 0.63 g of the desired compound(44%).

The NMR spectra of the desired compound were the same as those of the compound prepared in Example 13.

EXAMPLE 73

Synthesis of
(6R,7R)-7-[(Z)-2-(2-aminothiazol-4-yl)-2-methoxyiminoacetamido]-3-[(1-aminotetrazol-4-ium)methyl]-ceph-3-em-4-carboxylate By following the procedure in Example 71 except that 0.34 g(4 mmol) of 1-aminotetrazole was employed in place of 4-amino-1,2,4-triazole, there was obtained 0.6 g of the desired compound(41%).

The NMR spectra of the desired compound were the same as those of the compound prepared in Example 16.

EXAMPLE 74

Synthesis of
(6R,7R)-7-[(Z)-2-(2-aminothiazol-4-yl)-2-methoxyiminoacetamido]-3-[(2-amino-1,2,3,4-tetrahydroisoquinolin-2-ium)methyl]-ceph-3-em-4-carboxylate In 6 ml of dry dichloromethane was suspended 0.59 g(1.3 mmol) of (6R,7R)-7-[(Z)-2-(2-aminothiazol-4-yl)-2-methoxyiminoacetamido]-3-acetoxymethyl-ceph-3-em-4-carboxylic acid, 1.21 ml(6.5 mmol) of N,O-bis-trimethylsilyl trifluoroacetamide was added thereto under gaseous nitrogen atmosphere and the mixture was stirred at room temperature for 1 hour. 0.5 ml(3.5 mmol) of iodotrimethylsilane was added, and the resulting mixture was stirred at room temperature for 30 min. and concentrated under the reduced pressure. The residue was dissolved in 6 ml of dry acetonitrile, 0.9 ml of dry tetrahydrofuran was added thereto and the mixture was stirred for 10 min. 0.27 g(2 mmol) of 2-amino-1,2,3,4-tetrahydroisoquinoline and 1 ml of dry dichloromethane were added and the reaction mixture was stirred at room temperature for 3 hours. After completion of reaction, 0.3 ml of water was added under cooling. The resulting precipitate was filtered, washed with a mixed solvent of acetonitrile and diethyl ether, dried and suspended in a small amount of water, after which the pH was adjusted to 5~6 with saturated sodium bicarbonate solution. Then, purification was effected by HP-20 (Mitsubishi) column chromatography using 8% aqueous ethanol as an eluent. The fractions containing the desired product were concentrated under the reduced pressure and freeze-dried to give 268 mg of the desired compound(38%).

The NMR spectra of the desired compound were the same as those of the compound prepared in Example 5.

EXAMPLE 75

Synthesis of
(6R,7R)-7-[(Z)-2-(2-aminothiazol-4-yl)-2-methoxyiminoacetamido]-3-(1-aminoindoliniummethyl)ceph-3-em-4-carboxylate By following the procedure in Example 74 except that 0.27 g(2 mmol) of 1-aminoindoline was employed in place of 2-amino-1,2,3,4-tetrahydroisoquinoline, there was obtained 0.23 g of the desired compound(34%).

The NMR spectra of the desired compound were the same as those of the compound prepared in Example 6.

EXAMPLE 76

Synthesis of
(6R,7R)-7-[(Z)-2-(2-aminothiazol-4-yl)-2-methoxyiminoacetamido]-3-](1-aminobenzotriazol-3-ium) methyl]-ceph-3-em-4-carboxylate In 6 ml of dry dichloromethane was suspended 0.59 g(1.3 mmol) of (6R,7R)-7-[(Z)-2-(2-aminothiazol-4-yl)-2-methoxyiminoacetamido]-3-acetoxymethyl-ceph-3-em-4-carboxylic acid, 1.21 ml(6.5 mmol) of N,O-bis-trimethylsilyl trifluoroacetamide was added thereto under gaseous nitrogen atmosphere and the mixture was stirred at room temperature for 1 hour. 0.5 ml(3.5 mmol) of iodotrimethylsilane was added, and the reaction mixture was stirred at room temperature for 30 min and concentrated under the reduced pressure. The residue was dissolved in 6 ml of dry acetonitrile, 0.9 ml of dry tetrahydrofuran was added thereto and the mixture was stirred for 10 min. 0.296 g(2.2 mmol) of 1-aminobenzotriazole and 3 ml of dry dichloromethane were added and the reaction mixture was stirred at room temperature for 5 hours. After completion of reaction, 0.3 ml of water was added under cooling. The resulting precipitate was filtered, washed with a mixed solvent of acetonitrile and diethyl ether, dried, suspended in a small amount of water and the pH was adjusted to 4~4.5 with saturated sodium bicarbonate solution. Purification was effected by HP-20 (Mitsubishi) column chromatography using 15% aqueous acetonitrile as an eluent. The fractions containing the desired product were concentrated under the reduced pressure and freeze-dried to give 255 mg of the desired compound (37%).

The NMR spectra of the desired compound were the same as those of the compound prepared in Example 18.

EXAMPLE 77

Synthesis of (6R,7R)-7-[(Z)-2-(2-aminothiazol-4-yl)-2-methoxyiminoacetamido]-3-[(1-aminobenzimidazol-3-ium)methyl]-ceph-3-em-4-carboxylate By following the procedure in Example 76 except that 0.29 g(2.2 mmol) of 1-aminobenzimidazole was employed in place of 1-aminobenzotriazole, there was obtained 0.29 g of the desired compound(42%).

The NMR spectra of the desired compound were the same as those of the compound prepared in Example 19.

EXAMPLE 78

Synthesis of (6R,7R)-7-[(Z)-2-(2-aminothiazol-4-yl)-2-methoxyiminoacetamido]-3-[(1-amino-1,4,5,6-tetrahydropyrimidin-3-ium)methyl]-ceph-3-em-4-carboxylate By following the procedure in Example 76 except that 0.22 g(2.2 mmol) of 1-amino-1,4,5,6-tetrahydropyrimidine was employed in place of 1-aminobenzotriazole, there was obtained 0.2 g of the desired compound (31%).

The NMR spectra of the desired compound were the same as those of the compound prepared in Example 21.

PREPARATION EXAMPLE 7

Synthesis of 4-methoxybenzyl 7 β-(2-hydroxybenzylideneamino)-3-chloromethyl-ceph-3-em-4-carboxylate In 50 ml of methanol was dissolved 4.05 g(10 mmol) of 4-methoxybenzyl 7 β-amino-3-chloromethyl-ceph-3-em-4-carboxylate hydrochloride, and 1.28 ml(12 mmol) of salicylaldehyde and 1.39 ml(10 mmol) of triethylamine were added thereto. The reaction mixture was stirred for 5 hours. The resulting precipitate was filtered, washed with 50 ml of methanol and dried to give 4.26 g of the desired compound(90%).

NMR (DMSO-$d_6$, δ) 3.7 (d, 2H, C-2), 3.77 (s, 3H, OCH$_3$) 4.53 (s, 2H), 5.22 (s, 2H) 5.35 (d, 1H), 5.66 (d, 1H), 6.85~7.58 (m, 8H, phenyl) 8.75 (s, 1H)

PREPARATION EXAMPLE 8

Synthesis of 4-methoxybenzyl 7 β-(2-hydroxybenzylideneamino)-3-[(1-aminobenzotriazol-3-ium)methyl]-ceph-3-em-4-carboxylate iodide To 50 ml of acetone was added 4.73 g(10 mmol) of 4-methoxybenzyl 7 β-(2-hydroxybenzylideneamino)-3-chloromethyl-ceph-3-em-4-carboxylate prepared in Preparation Example 7 and 1.6 g(10.7 mmol) of sodium iodide was added thereto. The mixture was stirred for 3 hours in the darkness, concentrated under the reduced pressure to remove acetone. The concentrate was dissolved in acetonitrile(4.8 ml), and 1.07 ml(10 mmol) of salicylaldehyde and 4.3 g(30 mmol) of 1-aminobenzotriazole were added thereto and the mixture was stirred at 20°~25° C. for 24 hours. To the reaction solution was added 50 ml of acetone and the insoluble was filtered off. A mixture of diisopropyl ether (500 ml) and diethyl ether (500 ml) was added to the filtrate. The resulting precipitate was filtered and dried to give 6.28 g of the desired compound (90%).

NMR (DMSO-$d_6$, δ) 3.76 (s, 5H, OCH$_3$, C-2), 5.27 (s, 2H) 5.43 (d, 1H, C-6), 5.82 (d, 1H, C-7) 5.9 (q, 2H, C-3), 6.8~7.6 (m, 8H, phenyl) 8.0~8.33 (m, 4H), 8.83 (s, 1H)

PREPARATION EXAMPLE 9

Synthesis of 4-methoxybenzyl 7 β-amino-3-[(1-aminobenzotriazol-3-ium)methyl]-ceph-3-em-4-carboxylate iodide To 25 ml of acetonitrile was added 7 g (10 mmol) of 4-methoxybenzyl 7 β-(2-hydroxybenzylideneamino)-3-[(1-aminobenzotriazol-3-ium)methyl]-ceph-3-em-4-carboxylate iodide prepared in the above Preparation Example 8, and 10 ml of conc.hydrochloric acid was slowly added thereto at 0°~5° C. To the reaction mixture was added 100 ml of isopropyl alcohol, and the resulting precipitate was filtered and dried to give 5 g of the desired compound (80%).

NMR (DMSO-$d_6$, δ) 3.74 (s, 5H, OCH$_3$, C-2), 5.23 (bs, 2H) 5.4 (s, 2H, C-6, C-7), 5.95 (q, 2H, C-3) 6.8~7.3 (m, 4H, phenyl), 8.0~8.27 (m, 4H)

PREPARATION EXAMPLE 10

Synthesis of 4-methoxybenzyl (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate iodide To a mixture of phosphorus oxychloride (1.21 ml, 12 mmol) and ethyl acetate (40 ml) was added 2.21 g(11 mmol) of (Z)-2-(2-aminothiazol-4-yl)-2-methoxyiminoacetic acid and the mixture was stirred at 2°~6° C. for 30 min. 1.12 ml(12 mmol) of further phosphorus oxychloride was added and the mixture was stirred at 4°~6° C. for 30 min. 0.93 ml(12 mmol) of N,N-dimethylformamide was added and the mixture was stirred at the same temperature for 1 hour. Thus obtained solution was added to a solution of 6.31 g(10 mmol) of 4-methoxybenzyl 7 β-amino-3-[(1-aminobenzotriazol-3-ium)methyl]-ceph-3-em-4-carboxylate iodide prepared in Preparation Example 9 and 14.8 ml(60 mmol) of N,O-bis-trimethylsilyacetamide in 40 ml of ethyl acetate at −10°~5° C. and the mixture was stirred at −5° C. for 30 min. To the reaction solution were added 100 ml of ethyl acetate and 50 ml of water and the pH was adjusted to 6~7 with sodium bicarbonate. The organic layer was dried over anhydrous magnesium sulfate, concentrated under the reduced pressure and 300 ml of diisopropyl ether was added. The resulting precipitate was filtered and dried to give 5.8 g of the desired compound (75%).

NMR (DMSO-$d_6$, δ) 3.28~3.85 (m, 5H, C-2, OCH$_3$), 3.9 (s, 3H, OCH$_3$) 5.1 (d, 1H), 5.27 (bs, 2H), 5.6~6.0 (m, 3H) 6.8~7.3 (m, 5H, phenyl, thiazole-H) 8.0~8.3 (m, 4H)

EXAMPLE 79

Synthesis of (6R,7R)-7-[(Z)-2-(2-aminothiazol-4-yl)-2-methoxyiminoacetamide]-3-[(1-aminobenzotriazol-3-ium)methyl]-ceph-3-em-4-carboxylate.

To a mixture of trifluoroacetic acid (15 ml) and anisole (7.5 ml) was added 7.8 g(10 mmol) of 4-methoxybenzyl (6R,7R)-7-[(Z)-2-(2-aminothiazol-4-yl)-2-methoxyliminoaetamido]-3-[(1-aminobenzotriazol-3-ium)methyl]-ceph-3-em-4-carboxylate iodide prepared in Preparation Example 10 and the mixture was stirred at 35° C. for 4 hours. The reaction solution was concentrated under the reduced pressure and added to 500 ml of diethyl ether. The resulting precipitate was filtered, water was added thereto and the pH was adjusted to 4~4.5. Purification was effected by HP-20 column chromatography using 12% aqueous ethanol as an eluent. The fractions containing the desired product was concentrated under the reduced pressure and freeze-dried to give 3.9 g of the desired compound (75%).

The NMR spectra of the desired compound were the same as those of the compound prepared in Example 18.

PREPARATION EXAMPLE 11

Synthesis of 7 β-amino-3-[(1-aminobenzotriazol-3-ium)methyl]-ceph-3-em-4-carboxylate In a mixture of trifluoroacetic acid (15 ml) and anisole (7.5 ml) was dissolved 6.3 g(10 mmol) of 4-methoxybenzyl 7 β-amino-3-[(1-aminobenzotriazol-3-ium)methyl]-ceph-3-em-4-carboxylate iodide and the solution was stirred at 30°~35° C. for 4 hours. The reaction solution was concentrated under the reduced pressure, 500 ml of diisopropyl ether was added, and the resulting precipitate was filtered and dried. To the solid was added water and purification was effected by HP-20 column chromatography using 15% aqueous ethanol as an eluent. The fractions containing the desired product were concentrated under the reduced pressure and freeze-dried to give 2.6 g of the desired compound(75%).

NMR (DMSO-$d_6$, δ) 3.7 (m, 2H, C-2), 5.2 (m, 2H, C-6, C-7) 6.0 (q, 2H, C-3), 7.9~8.4 (m, 4H)

EXAMPLE 80

Synthesis of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate To a mixture of phosphorus oxychloride (1.12 ml, 12 mmol) and ethyl acetate(40 ml) was added 2.21 g(11 mmol) of (Z)-2-(2-aminothiazol-4-yl)-2-methoxyiminoacetic acid and the mixture was stirred at 2°~6° C. for 30 min. Further 1.21 ml(12 mmol) of phosphorus oxychloride was added and the resulting mixture was stirred at 4°~6° C. for 30 min. To the reaction solution was added 0.93 ml(12 mmol) of N,N-dimethylformamide and the mixture was stirred at the same temperature for 1 hour.

In 40 ml of ethyl acetate were dissolved 3.5 g(10 mmol) of 7 β-amino-3-[(1-aminobenzotriazol-3-ium)methyl]-ceph-3-em-4-carboxylate prepared in Preparation Example 11 and 14.8 ml(60 mmol) of N,O-bistrimethyl-silylacetamide, the solution prepared in the above was slowly added thereto at −10°~−5° C. and the mixture was stirred at −5° C. for 30 min. After confirming the completion of reaction, 10 ml of methanol was added and the solution was concentrated under the reduced pressure. To the residue was added water, the pH was adjusted to 4~4.5 and purification was effected by HP-20 column chromatography using 12% aqueous ethanol as an eluent. The fractions containing the desired product were concentrated under the reduced pressure and freeze-dried to give 3.7 g of the desired compound(70%).

The NMR spectra of the desired compound were the same as those of the compound obtained in Example 18.

PREPARATION EXAMPLE 12

Synthesis of 4-methoxybenzyl (6R,7R)-7-[(Z)-2-(2-tritylaminothiazol-4-yl)-2-methoxyiminoacetamido]-3-[(1-aminobenzotriazol-3-ium)methyl]-ceph-3-em-4-carboxylate iodide In 15 ml of dichloromethane was suspended 0.63 g(3 mmol) of phosphorus pentachloride and the suspension was cooled to −30° C. 1.2 g(2.5 mmol) of (Z)-2-(2-tritylaminothiazol-4-yl)-2-methoxyiminoacetic acid hydrochloride was added slowly and the mixture was stirred at −20°~−15° C. for 2 hours. 1.63 g(2.75 mmol) of 4-methoxybenzyl 7 β-amino-3-[(1-aminobenzotriazol-3-ium)methyl]-ceph-3-em-4-carboxylate iodide obtained in the above Preparation Example 9 was added to 30 ml of acetonitrile, 2.22 ml(9 mmol) of N,O-bistrimethylsilyl acetamide was added thereto and the mixture was stirred at 10°~15° C. for 1.5 hours. To this reaction solution was slowly added the solution obtained in the above at −30°~−25° C., the mixture was stirred at −20°~−15° C. for 1.5 hours and 20 ml of water and 40 ml of ethyl acetate were added. The organic layer was washed with saturated sodium bicarbonate solution and with saturated brine. The organic layer was dried over anhydrous sodium sulfate and the solid was filtered off. The filtrate was concentrated under the reduced pressure, and dichloromethane and diethyl ether were added. The resulting precipitate was filtered and dried to give 1.68 g of the desired compound(60%).

NMR (DMSO-$d_6$, δ) 3.6~3.8 (m, 2H, C-2), 3.83 (s, 3H) 3.87 (s, 3H), 5.13 (d, 1H), 5.3 (bs, 2H) 5.8~6.1 (m, 3H), 6.87 (s, 1H, thiazole-H) 6.9~7.5 (m, 19H), 7.6~7.9 (m, 4H)

EXAMPLE 81

Synthesis of (6R,7)-7-[(Z)-2-(2-aminothiazol-4-yl)-2-methoxyiminoacetamido]-3-[(1-aminobenzotriazol-3-ium)methyl]-ceph-3-em-4-carboxylate To 1.0 g(1 mmol) of 4-methoxybenzyl (6R,7R)-7-[(Z)-2-(2-tritylaminothiazol-4-yl)-2-methoxyiminoacetamido]-3-[(1-aminobenzotriazol-3-ium)methyl]-ceph-3-em-4-carboxylate iodide prepared in the above Preparation Example 12 were added 2 ml of trifluoroacetic acid and 1 ml of anisole, the mixture was stirred at 15°~20° C. for 2 hours and concentrated under the reduced pressure to remove trifluoroacetic acid. Diisopropyl ether was added, the resulting precipitate was filtered and dissolved in 5 ml of methanol. The insoluble was filtered off and the filtrate was concentrated under the reduced pressure. A small amount of water was added to the residue, the pH was adjusted to 4~4.5 and purification was effected by HP-20 column chromatography using 12% aqueous ethanol as an eluent. The fractions containing the desired compound were concentrated under the reduced pressure and freeze-dried to give 0.4 g of the desired compound(75%).

The NMR spectra of the desired compound were the same as those of the compound obtained in Example 18.

PREPARATION EXAMPLE 13

Synthesis of diphenylmethyl (6R,7R)-7-[(Z)-2-(2-tritylaminothiazol-4-yl)-2-methoxyiminoacetamido]-3-[(4-amino-1,2,4-triazol-2-ium)methyl]-ceph-3-em-4-carboxylate iodide By following the procedure in Preparation Example 12 except that 1.62 g(2.75 mmol) of diphenylmethyl 7 β-amino-3-[(4-amino-1,2,4-triazol-2-ium)methyl]-ceph-3-em-4-carboxylate iodide was employed in place of 4-methoxybenzyl 7 β-amino-3-[(1-aminobenzotriazol-3-ium)methyl]-ceph-3-em-4-carboxylate iodide, there was obtained 1.78 g of the desired compound (70%).

NMR (DMSO-d$_6$, δ) 3.4∼3.6 (m, 2H), 3.78 (s, 3H) 5.2 (d, 1H), 5.5∼5.9 (m, 3H) 6.8 (s, 1H), 7.1 (s, 1H) 7.1∼7.6 (m, 25H), 8.5, 9.3 (s, s, 2H)

EXAMPLE 82

Synthesis of (6R,7R)-7-[(Z)-2-(2-aminothiazol-4-yl)-2-methoxyiminoacetamido]-3-[(4-amino-1,2,4-triazol-2-ium)methyl]-ceph-3-em-4-carboxylate By following the procedure in Example 81 except that 1.0 g(1 mmol) of the compound prepared in the above Preparation Example 13 was employed, there was obtained 0.37 g of the desired compound(78%).

The NMR spectra of the desired compound were the same as those of the compound obtained in Example 12.

EXAMPLE 83

Synthesis of (6R,7R)-7-[(Z)-2-(5-amino-1,2,4-thiadiazol-3-yl)-2-carboxymethoxyiminoacetamido]-3-[(1-aminobenzotriazol-3-ium)methyl]-ceph-3-em-4-carboxylate By following the procedure in Example 60 except that 0.5 g(1 mmol) of (6R,7R)-7-[(Z)-2-(5-amino-1,2,4-thiadiazol-3-yl)-2-carboxymethoxyiminoacetamido]-3-acetoxymethyl-ceph-3-em-4-carboxylic acid was employed in place of (6R,7R)-7-[(Z)-2-(2-aminothiazol-4-yl)-2-carboxymethoxyiminoacetamido]-3-acetoxymethyl-ceph-3-em-4-carboxylic acid, there was obtained 0.15 g of the desired compound(26%).

MS(FAB, M+1)=575

NMR(DMSO-d$_6$+20% DCl, δ) 3.8∼4.0 (m, 2H), 4.73 (s, 2H) 5.1∼5.52 (m, 3H), 5.82 (d, 1H) 7.5∼8.2 (m, 4H)

EXAMPLE 84

Synthesis of (6R,7R)-7-[(Z)-2-(5-amino-1,2,4-thiadiazol-3-yl)-2-(2-carboxyprop-2-oxyimino)acetamido]-3-[(1-aminobenzotriazol-3-ium)methyl]-ceph-3-em-4-carboxylate By following the procedure in Example 49 except that 0.57 g (1.09 mmol) of (6R,7R)-7-[(Z)-2-(5-amino-1,2,4-thiadiazol-3-yl)-2-(2-carboxyprop-2-oxyimino)acetamido]-3-acetoxymethyl-ceph-3-em-4-carboxylic acid was employed, there was obtained 0.12 g of the desired compound (20%).

MS(FAB, M+1)=603

NMR(DMSO-d$_6$+20% DCl, δ) 1.3 (d, 6H), 3.86∼4.1 (m, 2H) 5.05∼5.55 (m, 3H), 5.8 (d, 1H) 7.5∼8.1 (m, 4H)

EXAMPLE 85

Synthesis of (6R,7R)-7-[(Z)-2-(5-amino-1,2,4-thiadiazol-3-yl)-2-methoxyiminoacetamido]-3-[(1-aminobenzotriazol-3-ium)methyl]-ceph-3-em-4-carboxylate In a mixture of acetonitrile (1 ml) and water (1.5 ml) was dissolved 0.67 g(5 mmol) of lithium iodide and the solution was heated to 65°∼67° C. 0.24 g(1.8 mmol) of 1-aminobenzotriazole and 0.46 g(1 mmol) of (6R,7R)-7-[(Z)-2-(5-amino-1,2,4-thiadiazol-3-yl)-2-methoxyiminoacetamido]-3-acetoxymethyl-ceph-3-em-4-carboxylic acid were added and the mixture was stirred at 70° C. for 1 hour while adjusting its pH to 6.8∼7.1. After completion of reaction, the reaction solution was cooled to room temperature and stirred for 30 min while adjusting the pH to 1∼1.5 with 3N hydrochloric acid. The insoluble was filtered off, the filtrate was concentrated under the reduced pressure and subjected to column chromatography over aluminium oxide and over silica gel using 80% aqueous acetonitrile as an eluent. The fractions were concentrated under the reduced pressure, dissolved in a small amount of water and purified by HP-20(Mitsubishi) column chromatography using 15% aqueous ethanol as an eluent. The fractions containing the desired product were concentrated under the reduced pressure and freeze-dried to give 0.14 g of the desired compound in a pale yellowish white amorphous form (26.4%).

MS(FAB, M+1)=531

NMR(DMSO-d$_6$+20% DCl, δ) 3.8∼4.0 (m, 2H), 4.05 (s, 3H) 5.1∼5.6 (m, 3H), 5.85 (d, 1H) 7.6∼8.1 (m, 4H)

EXAMPLE 86

Synthesis of (6R,7R)-7-[(Z)-2-(5-amino-1,2,4-thiadiazol-3-yl)-2-methoxyiminoacetamido]-3-[(1-aminobenzimidazol-3-ium)methyl]-ceph-3-em-4-carboxylate By following the procedure in Example 85 except that 0.24 g(1.8 mmol) of 1-aminobenzimidazole was employed in place of 1-aminobenzotriazole, there was obtained 0.13 g of the desired compound (24%).

MS(FAB, M+1)=530

NMR(DMSO-d$_6$, δ) 3.3∼3.7 (m, 2H), 3.8 (s, 3H) 5.05 (d, 1H), 5.4∼5.85 (m, 3H) 7.5∼8.5 (m, 4H), 10.1 (s, 1H)

EXAMPLE 87

Synthesis of (6R,7R)-7-[(Z)-2-(5-amino-1,2,4-thiadiazol-3-yl)-2-methoxyiminoacetamido]-3-[(1-amino-1,2,4-triazol-4-ium)methyl]-ceph-3-em-4-carboxylate By following the procedure in Example 85 except that 0.15 g(1.8 mmol) of 1-amino-1,2,4-triazole was employed in place of 1-aminobenzotriazole, there was obtained 0.14 g of the desired compound (29%).

MS(FAB, M+1)=481

NMR(DMSO-d$_6$+20% DCl, δ) 3.25∼3.7 (m, 2H), 3.8 (s, 3H) 5.1∼5.3 (m, 3H), 5.6 (d, 1H) 8.7, 9.7 (s,s, 2H)

EXAMPLE 88

Synthesis of
(6R,7R)-7-[(Z)-2-(2-aminothiazol-4-yl)-2-methoxyiminoacetamido]-3-[(1-aminobenzotriazol-3-ium)methyl]-ceph-3-carboxylate sulfate In 4 ml of water was dissolved 0.5 g(0.95 mmol) of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate prepared in Example 18, the solution was cooled to 5° C. and the pH was adjusted to 1~1.5 with 3N sulfuric acid. After stirring at the same temperature for 1 hour, 10 ml of isopropyl alcohol was added and the mixture was stirred at 0°~5° C. for 4 hours. The resulting precipitate was filtered, washed with isopropyl alcohol and diethyl ether and dried to give 0.54 g of the desired compound in a form of white crystalline solid (91%).

m.p.=176° C.~(decomp.)
MS(FAB, M+1)=628
NMR (DMSO-$d_6$, δ) 3.51 (q, 2H, C-2), 3.83 (s, 3H, $OCH_3$) 5.2 (d, 1H), 5.4~5.94 (m, 3H) 6.74 (s, 1H, thiazole-H) 8.02~8.52 (m, 6H), 9.6 (d, 1H)

EXAMPLE 89

Synthesis of
(6R,7R)-7-[(Z)-2-(2-aminothiazol-4-yl)-2-methoxyiminoacetamido]-3-[(4-amino-1,2,4-triazol-2-ium)methyl]-ceph-3-em-4-carboxylate sulfate By following the procedure in Example 88 except that 0.2 g(0.42 mmol) of (6R,7R)-7-[(Z)-2-(2-aminothiazol-4-yl)-2-methoxyiminoacetamido]-3-[(4-amino-1,2,4-triazol-2-ium)methyl]-ceph-3-em-4-carboxylate prepared in Example 12 was employed in place of (6R,7R)-7[(Z)-2-(2-aminothiazol-4-yl)-2-methoxyiminoacetamido]-3-[(1-aminobenzotriazol-3-ium)methyl]-ceph-3-em-4-carboxylate, there was obtained 0.22 g of the desired compound (91.3%).

NMR (DMSO-$d_6$, δ) 3.5 (m, 2H, C-2), 3.83 (s, 3H, $OCH_3$) 5.1 (d, 1H, C-6), 5.4~5.85 (m, 3H, C-7, C-3) 6.75 (s, 1H, thiazole-H), 8.76, 9.81 (s,s, 2H, triazole)

EXAMPLE 90

Synthesis of
(6R,7R)-7-[(Z)-2-(2-aminothiazol-4-yl)-2-methoxyiminoacetamido]-3-[(1-aminobenzimidazol-3-ium)methyl]-ceph-3-em-4-carboxylate sulfate By following the procedure in Example 88 except that 0.25 g(0.47 mmol) of (6R,7R)-7-[(Z)-2-(2-aminothiazol-4-yl)-2-methoxyiminoacetamido]-3-[(1-aminobenzimidazol-3-ium)methyl]-ceph-3-em-4-carboxylate Prepared in Example 19 was employed in place of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate, there was obtained 0.26 g of the desired compound (88%).

NMR (DMSO-$d_6$, δ) 3.3~3.6 (m, 2H, C-2), 3.81 (s, 3H, $OCH_3$) 5.08 (d, 1H, C-6), 5.5~5.9 (m, 3H, C-7, C-3) 6.76 (s, 1H, thiazole-H), 7.5~8.4 (m, 4H, phenyl) 10.1 (s, 1H, imidazole)

EXAMPLE 91

Synthesis of
(6R,7R)-7-[(Z)-2-(2-aminothiazol-4-yl)-2-methoxyiminoacetamido]-3-[(1-aminobenzotriazol-3-ium) methyl]-ceph-3-em-4-carboxylate maleate In 1.5 ml of water was dissolved 0.15 g(0.28 mmol) of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate prepared in Example 18, the solution was cooled to 5°~10° C., 0.034 g(0.29 mmol) of maleic acid was added thereto and the mixture was stirred at 5° C. for 2 hours. A mixture of isopropyl alcohol (12 ml) and diethyl ether(3 ml) was added and the resulting mixture was stirred at 0°~5° C. for 5 hours. The resulting precipitate was filtered, washed with diethyl ether and dried to give 0.15 g of the desired compound in a form of white crystalline solid (82%).

m.p.=136° C.~(decomp.)
NMR (DMSO-$d_6$, δ) 3.55 (q, 2H, C-2), 3.85 (s, 3H, $OCH_3$) 5.19 (d, 1H), 5.4~5.96 (m, 3H) 6.06 (s, 2H), 6.75 (s, 1H, thiazole-H), 8.03~8.48 (m, 6H)

EXAMPLE 92

Synthesis of
(6R,7R)-7-[(Z)-2-(5-amino-1,2,4-thiadiazol-3-yl)-2-methoxyiminoacetamido]-3-[(1-aminobenzotriazol-3-ium) methyl]-ceph-3-em-4-carboxylate sulfate By following the procedure in Example 88 except that 0.5 g(0.94 mmol) of (6R,7R)-7-[(Z)-2-(5-amino-1,2,4-thiadizaol-3-yl)-2-methoxyiminoacetamido]-3-[(1-aminobenzotriazol-3-ium)methyl]-ceph-3-em-4-carboxylate prepared in Example 85 was employed in place of (6R,7R)-7-[(Z)-2-(2-aminothiazol-4-yl)-2-methoxyiminoacetamido]-3-[(1-aminobenzotriazol-3-ium)methyl]-ceph-3-em-4-carboxylate, there was obtained 0.51 g of the desired compound (86%).

NMR (DMSO-$d_6$, δ) 3.75~4.0 (m, 2H), 4.03 (s, 3H) 5.15 (d, 1H), 5.45~5.9 (m, 3H) 7.7~8.05 (m, 4H)

What we claim is:
1. A compound of the formula

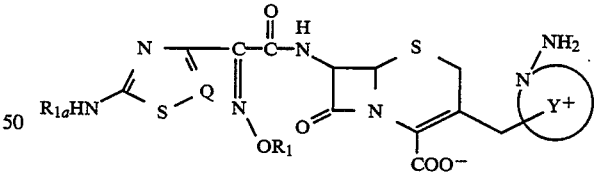

wherein,
$R_1$ represents a $C_1$~$C_4$ alkyl group or

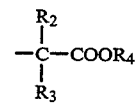

wherein, $R_2$ and $R_3$, independently, represent hydrogen or a $C_1$~$C_3$ alkyl group and $R_4$ represents hydrogen or a $C_1$~$C_4$ alkyl group;

$R_{1a}$ represents hydrogen or an amino-protecting group;

Q represents CH or N; and
the formula

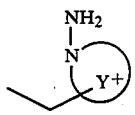

represents a substituent selected from the group consisting of:
1-aminopyrrolidinium methyl, 1-aminopiperidinium methyl,
(4-aminomorpholin-4-ium)methyl,
(1-amino-1,2,3,6-tetrahydropyridinium)methyl,
(1-amino-3-pyrrolin-1-ium)methyl,
1-aminoindolinium methyl,
1-aminopyrrolium methyl,
1-aminoindolium methyl,
(1-amino-4-hydroxypiperidinium)methyl,
(2-amino-1,2,3,4-tetrahydroisoquinolin-2-ium)methyl,
(1-amino-1-methyl-4-piperazinium)methyl,
(4-amino-1,2,4,-triazol-2-ium)methyl,
(1-amino-1,2,3-triazol-3-ium)methyl,
(1-amino-1,2,4-triazol-4-ium)methyl,
(1-aminobenzotriazol-3-ium)methyl,
(1-aminobenzimidazol-3-ium)methyl,
(1-aminoimidazol-3-ium)methyl,
(1-aminopyrazol-2-ium)methyl,
(1-aminotetrazol-4-ium)methyl,
(1-amino-1,4,5,6-tetrahydropyrimidin-3-ium)methyl and
(1-aminoindazol-2-ium)methyl,
or a pharmaceutically acceptable salt thereof; and mixtures thereof.

2. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen; Q is CH or N ; and

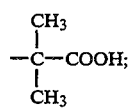

is 1-aminopyrrolidinium methyl, or a pharmaceutically acceptable salt thereof.

3. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen; Q is CH or N; and

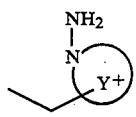

is (2-amino-1,2,3,4-tetrahydroisoquinolin-2-ium)methyl, or a pharmaceutically acceptable salt thereof.

4. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen ; Q is CH or N; and

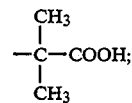

is (1-amino-1-methyl-4-piperazinium)methyl, or a pharmaceutically acceptable salt thereof.

5. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen ; Q is CH or N; and

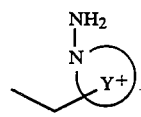

is (4-amino-1,2,4-triazol-2-ium)methyl, or a pharmaceutically acceptable salt thereof.

6. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen ; Q is CH or N; and

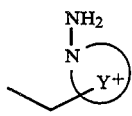

is (1-amino-1,2,3-triazol-3-ium)methyl, or a pharmaceutically acceptable salt thereof.

7. The compound according to claim 1, wherein $R_1$ is methyl, —CH$_2$COOH or $$-\underset{\underset{CH_3}{|}}{\overset{\overset{CH_3}{|}}{C}}-COOH;$$

$R_{1a}$ is hydrogen ; Q is CH or N; and

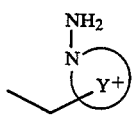

is (1-amino-1,2,4-triazol-4-ium)methyl, or a pharmaceutically acceptable salt thereof.

8. The compound according to claim 1, wherein $R_1$ is methyl, —$CH_2COOH$ or

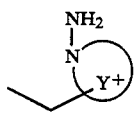

$R_{1a}$ is hydrogen ; Q is CH or N; and

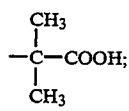

is (1-aminobenzotriazol-3-ium)methyl, or a pharmaceutically acceptable salt thereof.

9. The compound according claim 1, wherein, $R_1$ is methyl, —$CH_2COOH$ or

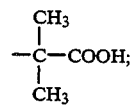

$R_{1a}$ is hydrogen ; Q is CH and N ; and

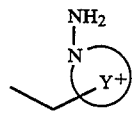

is (1-aminobenzimidazol-3-ium)methyl, or a pharmaceutically acceptable salt thereof.

10. The compound according to claim 1, wherein the pharmaceutically acceptable salt is a hydrochloride, sulfate or maleate salt of said compound.

11. An antibacterial composition which comprises an antibacterially-effective amount of at least one of the compounds according to claim 1 as an active ingredient, in association with a pharmaceutically acceptable additive therefor.

12. A method of treating an infectious disease, caused by bacterial infection in animals or humans which comprises administering an antibacterially effective amount of the compound as defined in claim 1.

13. A composition of claim 11 wherein said additive is a pharmaceutically-acceptable excipient.

14. A composition of claim 11 wherein said additive is a pharmaceutically-acceptable carrier.

* * * * *

UNITED STATES PATENT AND TRADEMARK OFFICE
CERTIFICATE OF CORRECTION

PATENT NO. : 5,336,673
DATED : August 9, 1994
INVENTOR(S) : Chi J. MOON et al.

It is certified that error appears in the above-indentified patent and that said Letters Patent is hereby corrected as shown below:

At column 3, line 62, change "e.g. methanesulfonate" to ---e.g., methanesulfonate---.
    At column 7, line 49, change "compound" to ---compounds---.
    At column 7, line 64, change "ethyldilisopropylamine" to ---ethyldiisopropylamine---.
    At column 13, line 64, change "the" to ---The---.
    At column 13, line 66, change "hot" to ---not---.
    At column 19, line 1, insert ---7.8(d, 2H)--- after "∂".
    At column 28, line 44, change "aminopiperidininiummethyl" to ---aminopiperidiniummethyl---.
    At column 39, line 21, change "(6R,7)" to ---(6R,7R)---.

Signed and Sealed this

Twenty-eight Day of March, 1995

*Attest:*

BRUCE LEHMAN

*Attesting Officer*     *Commissioner of Patents and Trademarks*